United States Patent [19]

Green et al.

[11] Patent Number: 5,573,541
[45] Date of Patent: Nov. 12, 1996

[54] APPARATUS AND METHOD FOR SUBCUTICULAR STAPLING OF BODY TISSUE

[75] Inventors: David T. Green, Westport; Henry Bolanos, East Norwalk, both of Conn.

[73] Assignee: United States Surgical Corporation, Norwalk, Conn.

[21] Appl. No.: 383,718

[22] Filed: Feb. 3, 1995

Related U.S. Application Data

[60] Division of Ser. No. 959,242, Oct. 9, 1992, Pat. No. 5,389,102, which is a continuation-in-part of Ser. No. 842,448, Feb. 27, 1992, Pat. No. 5,292,326, which is a continuation-in-part of Ser. No. 630,224, Dec. 19, 1990, abandoned, which is a continuation-in-part of Ser. No. 581,776, Sep. 13, 1990, abandoned.

[51] Int. Cl.$^6$ ................................................. A61B 17/04
[52] U.S. Cl. ..................... 606/143; 606/142; 606/213; 606/219; 227/177.1
[58] Field of Search ............................ 606/142, 143, 606/144, 151, 213, 219, 221; 227/176, 177, 19, 181, 197, 198

[56] References Cited

U.S. PATENT DOCUMENTS

| | | |
|---|---|---|
| 2,182 | 7/1841 | Spike . |
| 415,175 | 11/1889 | Prouty . |
| 715,612 | 12/1902 | Van Schott . |
| 816,026 | 3/1906 | Meier . |

(List continued on next page.)

FOREIGN PATENT DOCUMENTS

| | | |
|---|---|---|
| 256506 | 5/1963 | Australia . |
| 0173451 | 3/1986 | European Pat. Off. . |
| 0392750 | 10/1990 | European Pat. Off. . |
| 2308349 | 11/1976 | France . |
| 2740274 | 3/1978 | Germany . |

(List continued on next page.)

OTHER PUBLICATIONS

LaSutura Perde IL Filo.
Publication Entitled *Wood Repair*, Erie E. Peacock, pp. 141–158, dated 1984.
"United States Surgical Corporation Information Booklet for Auto Suture® Purse String Instrument", copyright 1977, 1978, United States Surgical Corporation.

*Primary Examiner*—Gary Jackson

[57] ABSTRACT

A surgical apparatus for attaching two portions of cutaneous body tissue includes a pair of opposed elongated members having jaws which have tissue gripping members thereon at one end and which are movable toward each other to a closed position to engage two body tissue portions positioned within the members to move the body tissue portions into close approximation. Manually gripping systems of several alternative configurations are provided to actuate a mechanical transmission system to close the jaws. In a preferred embodiment, a fork is movable from a first position to a second position by manually operable devices to move the jaws toward each other. A pair of cam faces is located adjacent the opposite ends of the jaws. As the fork moves to its second position, the tines of the fork engage against the cam faces to move the opposed jaws to their closed position. A plurality of rod-like fasteners are carried in a stacked configuration proximally of the jaws such that when the jaws are in their closed position and the two body tissue portions are held in close approximation. Each rod-like fastener is movable to a position in ingress to penetrate the body tissue portions to attach the body tissue portions together. In another preferred embodiment, the elongated members are biased outwardly by a coil spring and a unique plate-like fastener drive member is provided to facilitate driving a fastener after the jaws are closed. A fastener cartridge is provided with fasteners stacked in a sloped fashion and having a coil spring to bias the fasteners toward the ejection position. Another embodiment includes a rack and gear teeth arrangement for approximating the jaws and for firing the fasteners. The rack and gear teeth function somewhat like a linear analog of a set of rotary gears. A method of attaching cutaneous body tissue portions is also disclosed.

25 Claims, 29 Drawing Sheets

U.S. PATENT DOCUMENTS

| | | |
|---|---|---|
| 1,200,594 | 10/1916 | Curtis . |
| 1,452,373 | 4/1923 | Gomez . |
| 1,906,527 | 5/1933 | Bradley . |
| 1,933,317 | 10/1933 | Curtis . |
| 2,254,620 | 9/1941 | Miller . |
| 2,356,376 | 8/1944 | Brown, Jr. . |
| 2,668,538 | 2/1954 | Baker . |
| 2,811,971 | 11/1957 | Scott . |
| 2,910,067 | 10/1959 | White . |
| 3,110,899 | 11/1963 | Warren . |
| 3,150,379 | 9/1964 | Brown . |
| 3,203,220 | 8/1965 | Kaepernick . |
| 3,205,757 | 9/1965 | Kuennen . |
| 3,378,010 | 4/1968 | Codling et al. . |
| 3,526,257 | 9/1970 | Kirkland . |
| 3,618,447 | 11/1971 | Goins . |
| 3,631,707 | 1/1972 | Miller . |
| 3,716,058 | 2/1973 | Tanner, Jr. . |
| 4,052,988 | 10/1977 | Doddi et al. . |
| 4,064,881 | 12/1977 | Meredith . |
| 4,162,678 | 7/1979 | Fedotov et al. . |
| 4,164,225 | 8/1979 | Johnson et al. . |
| 4,256,251 | 3/1981 | Moshofsky . |
| 4,345,600 | 8/1982 | Rothfuss . |
| 4,399,810 | 8/1983 | Samuels et al. . |
| 4,406,392 | 9/1983 | Campbell et al. . |
| 4,448,194 | 5/1984 | DiGiovanni et al. . |
| 4,451,254 | 5/1984 | Dinius et al. . |
| 4,493,322 | 1/1985 | Becht . |
| 4,506,669 | 3/1985 | Blake, III . |
| 4,506,819 | 3/1985 | Rand . |
| 4,523,591 | 6/1985 | Kaplan et al. . |
| 4,523,695 | 6/1985 | Braun et al. . |
| 4,526,173 | 7/1985 | Sheehan . |
| 4,527,725 | 7/1985 | Foslien . |
| 4,527,726 | 7/1985 | Assell et al. . |
| 4,535,772 | 8/1985 | Sheehan . |
| 4,569,469 | 2/1986 | Mongeon et al. . |
| 4,591,086 | 5/1986 | Campbell et al. . |
| 4,595,007 | 6/1986 | Mericle . |
| 4,605,002 | 8/1986 | Rebuffat . |
| 4,610,251 | 9/1986 | Kumar . |
| 4,612,923 | 9/1986 | Kronenthal . |
| 4,688,560 | 8/1987 | Schulz . |
| 4,712,550 | 12/1987 | Sinnett . |
| 4,744,365 | 5/1988 | Kaplan et al. . |
| 4,753,636 | 6/1988 | Free . |
| 4,815,468 | 3/1989 | Annand . |
| 4,832,026 | 5/1989 | Jones . |
| 4,834,098 | 5/1989 | Jones . |
| 4,841,960 | 6/1989 | Garner . |
| 4,858,603 | 8/1989 | Clemow et al. . |
| 4,865,032 | 9/1989 | Jones . |
| 4,869,242 | 9/1989 | Galluzzo . |
| 4,873,976 | 10/1989 | Schreiber . |
| 4,874,122 | 10/1989 | Froehlich et al. . |
| 4,887,756 | 12/1989 | Puchy . |
| 4,895,148 | 1/1990 | Bays et al. . |
| 4,898,186 | 2/1990 | Ikada et al. . |
| 4,899,745 | 2/1990 | Laboureau et al. . |
| 4,924,866 | 5/1990 | Yoon . |
| 4,944,742 | 7/1990 | Clemow et al. . |
| 4,973,211 | 11/1990 | Potucek . |
| 4,976,686 | 12/1990 | Ball et al. . |
| 5,004,469 | 4/1991 | Palmieri et al. . |
| 5,007,921 | 4/1991 | Brown . |
| 5,026,374 | 6/1991 | Dezza et al. . |
| 5,047,047 | 9/1991 | Yoon . |
| 5,156,609 | 10/1992 | Nakao et al. . |
| 5,158,566 | 10/1992 | Pianetti . |

FOREIGN PATENT DOCUMENTS

| | | |
|---|---|---|
| 8522122 | 10/1985 | Germany . |
| 166352 | 3/1984 | Sweden . |
| 888965 | 12/1981 | U.S.S.R. . |
| 1210801 | 2/1986 | U.S.S.R. . |
| 873960 | 8/1961 | United Kingdom . |
| 1172775 | 12/1969 | United Kingdom . |
| 1350100 | 4/1974 | United Kingdom . |
| WO8503857 | 9/1985 | WIPO . |
| WO8901767 | 3/1989 | WIPO . |

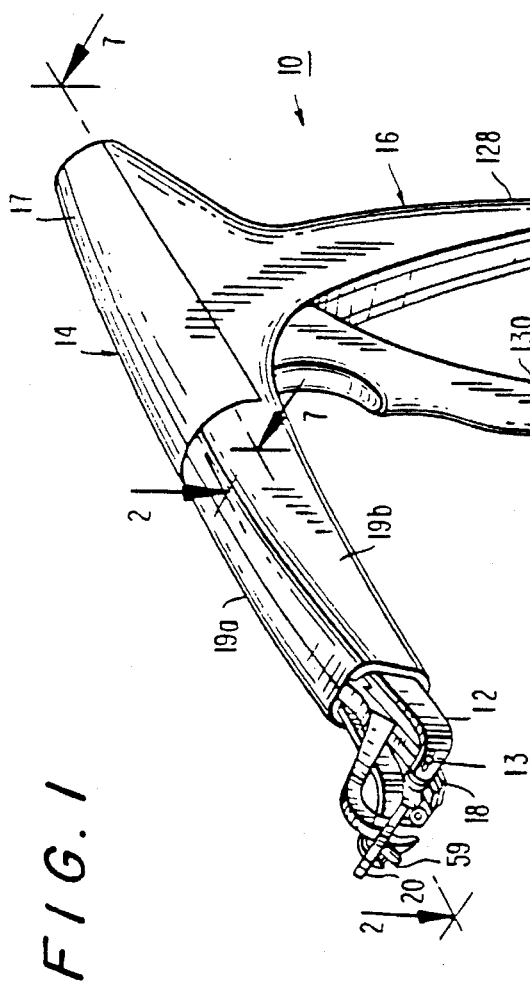
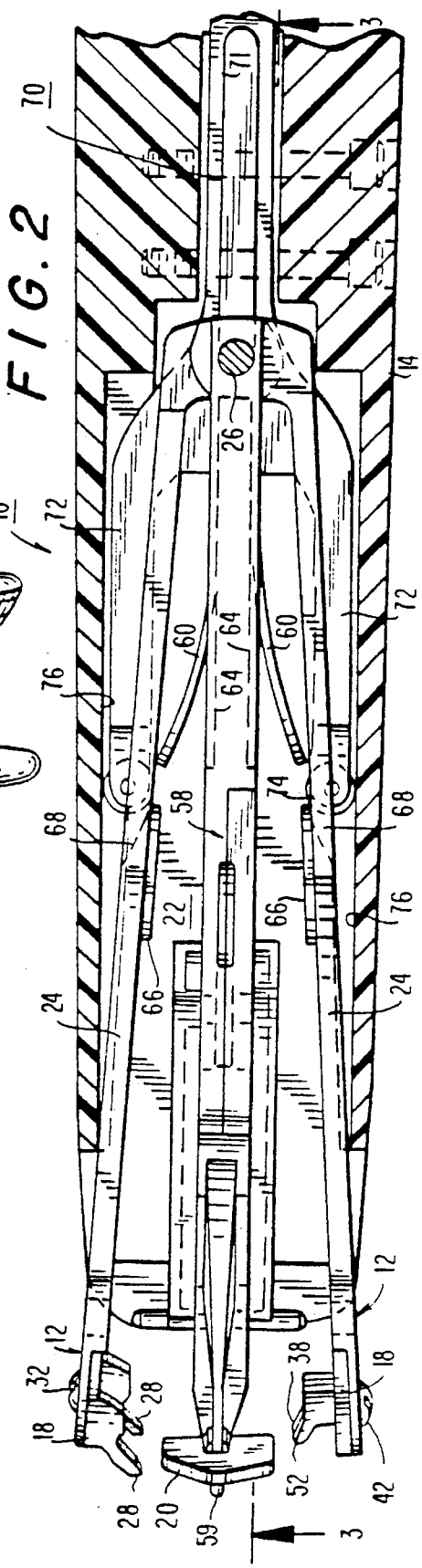

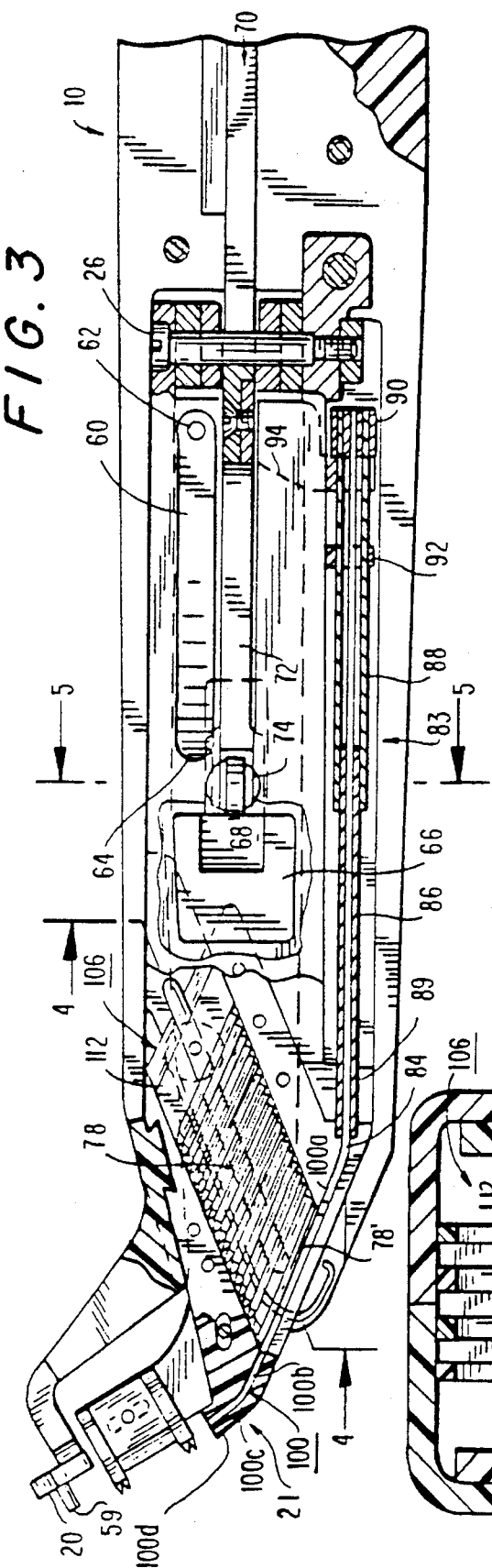
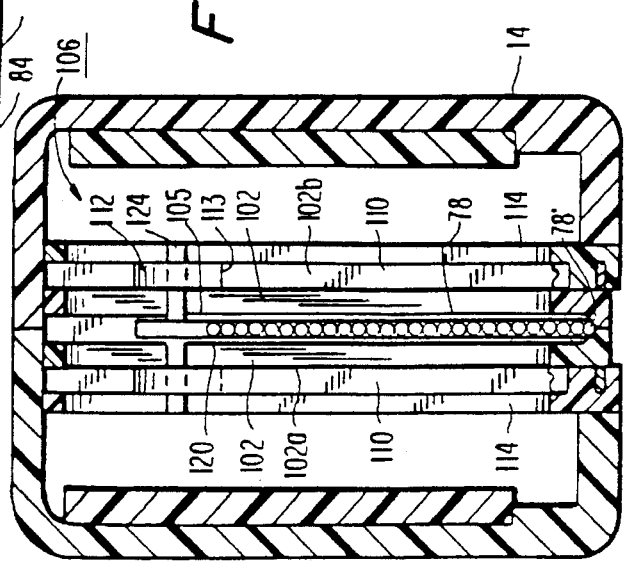
FIG. 3
FIG. 4
FIG. 5

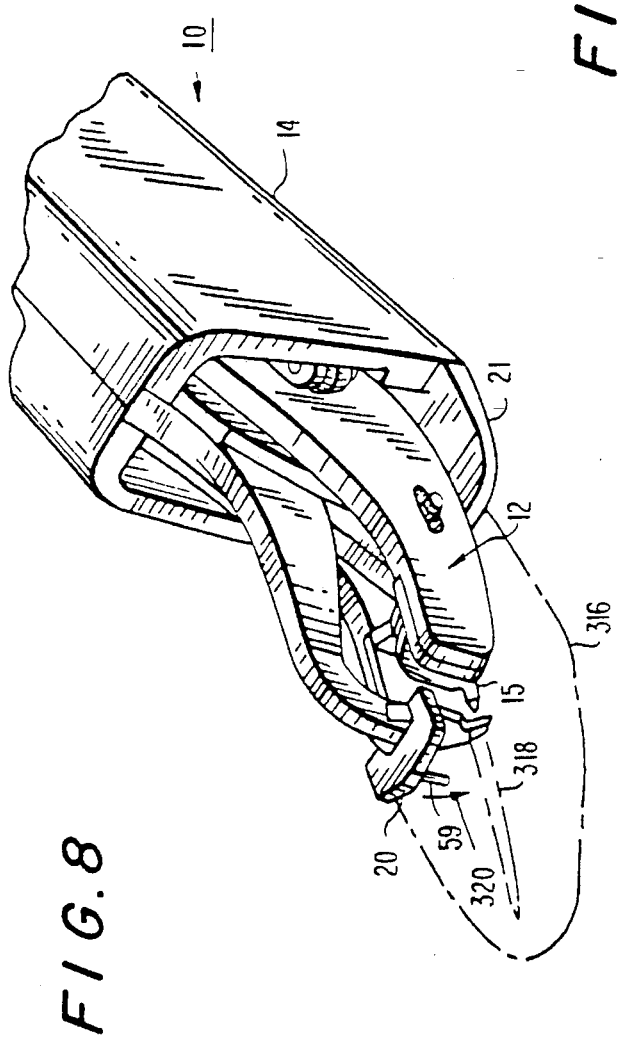
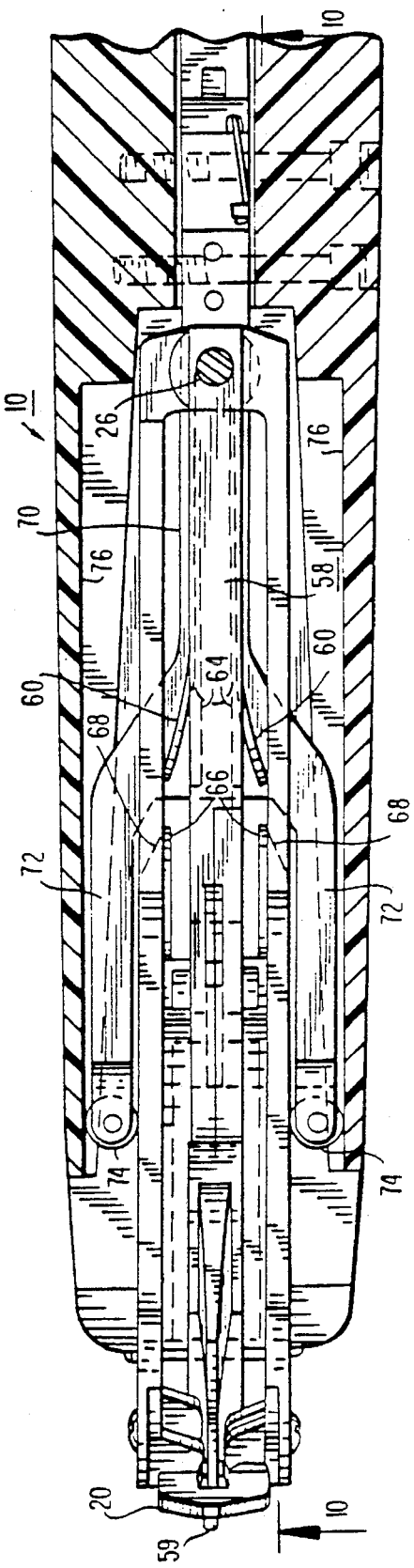
FIG. 8
FIG. 9

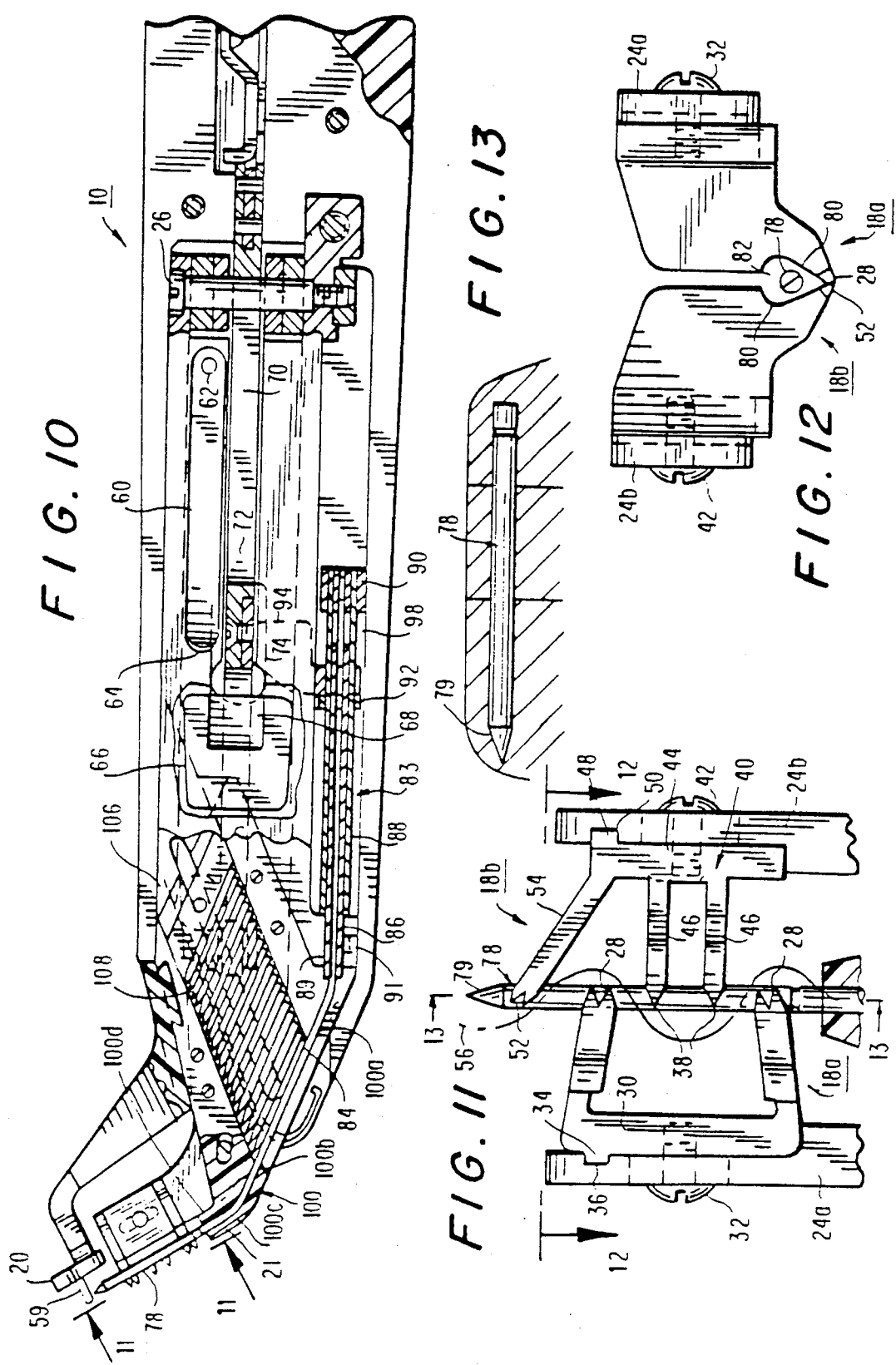

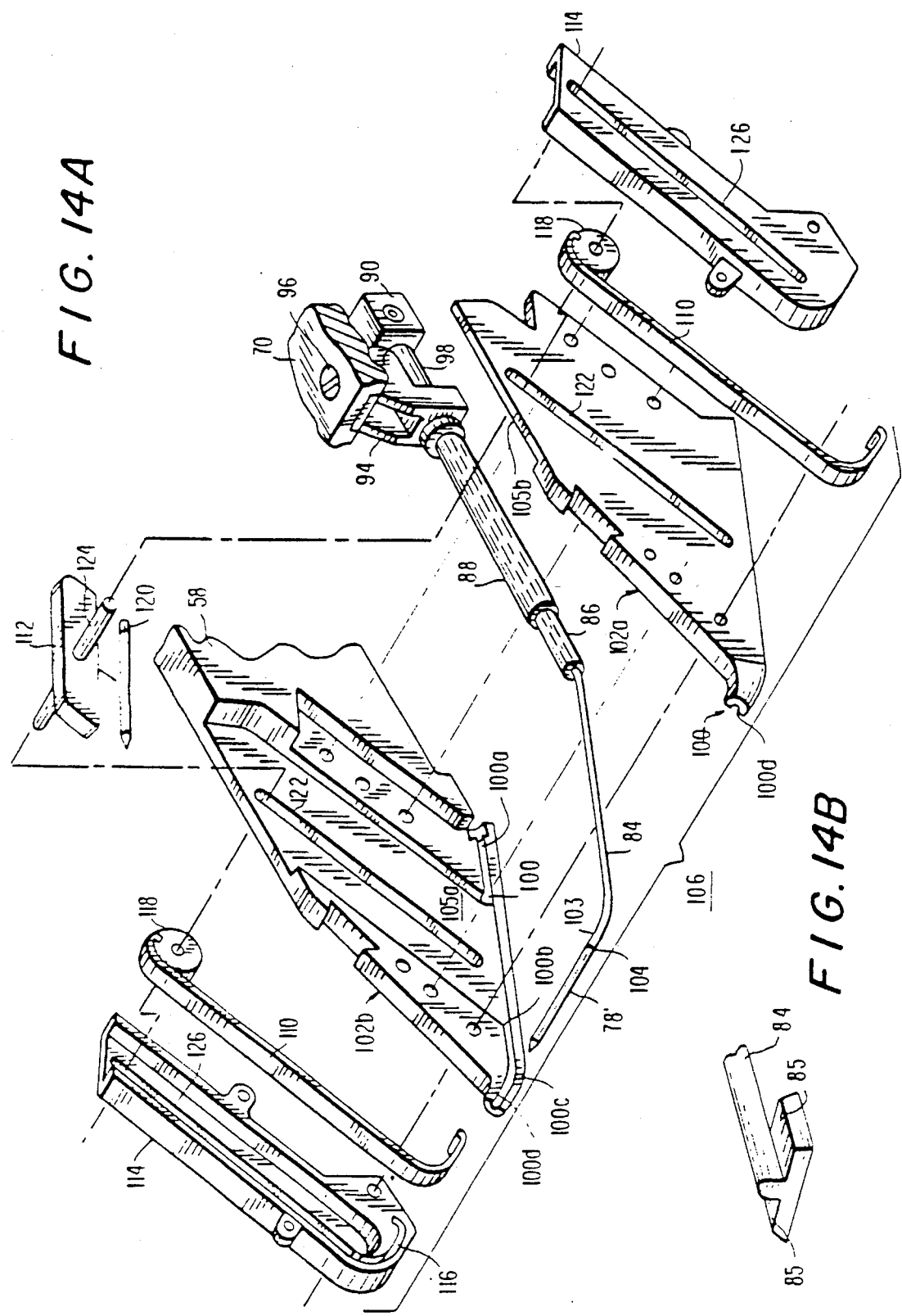

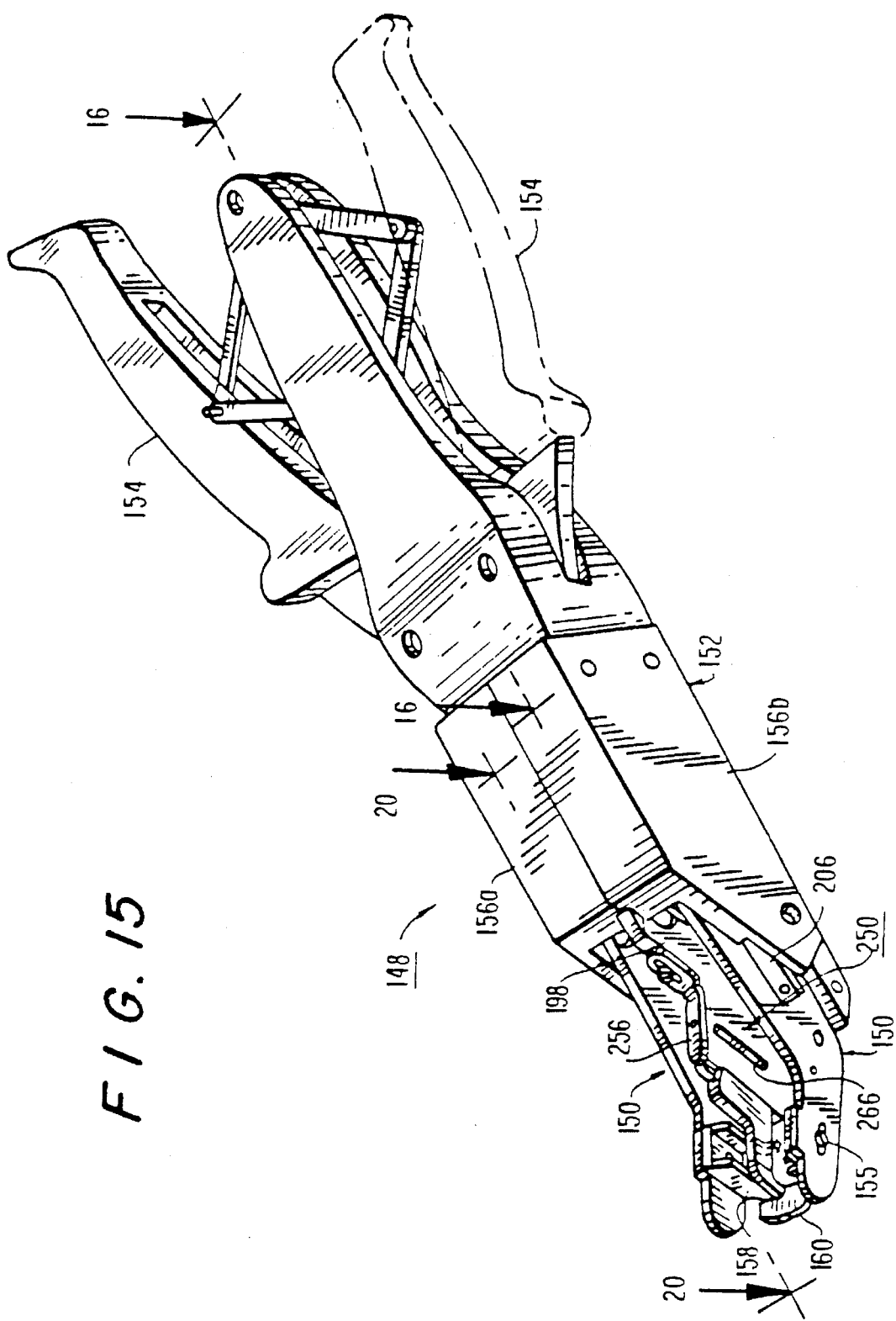

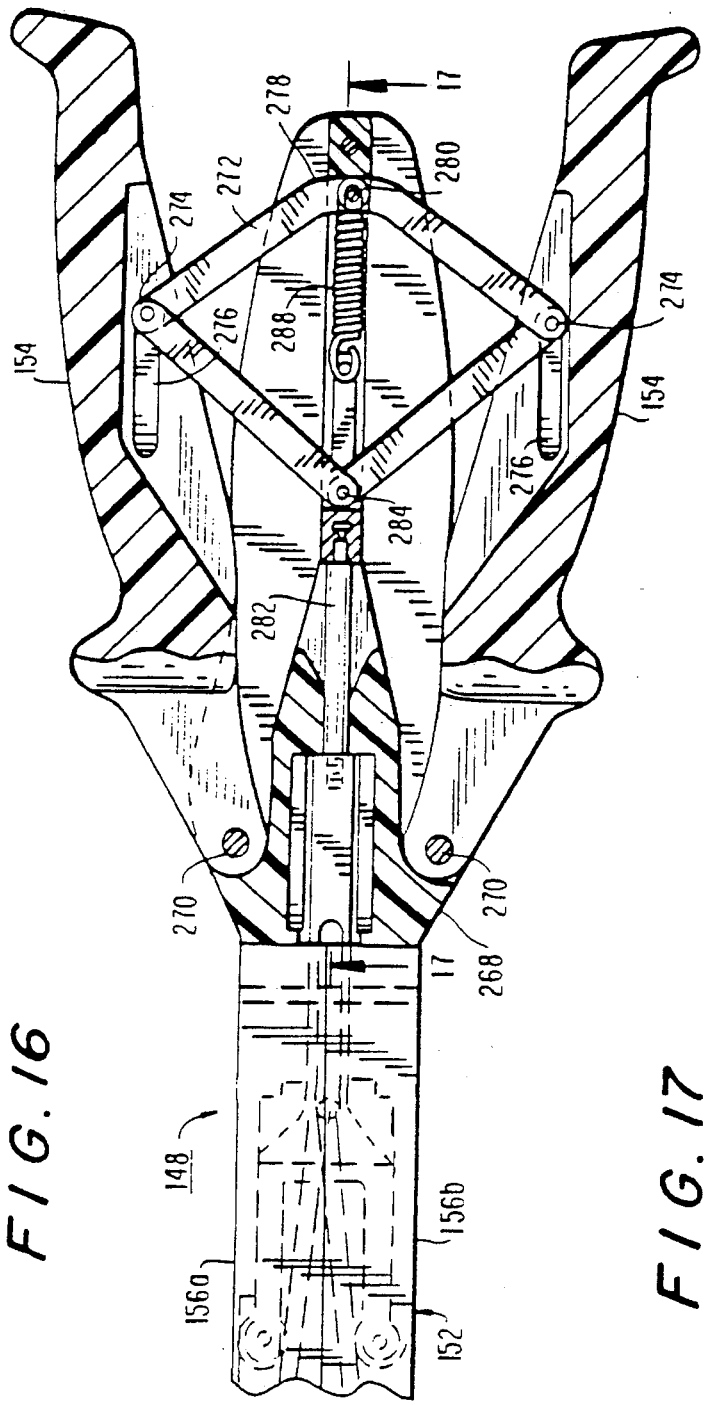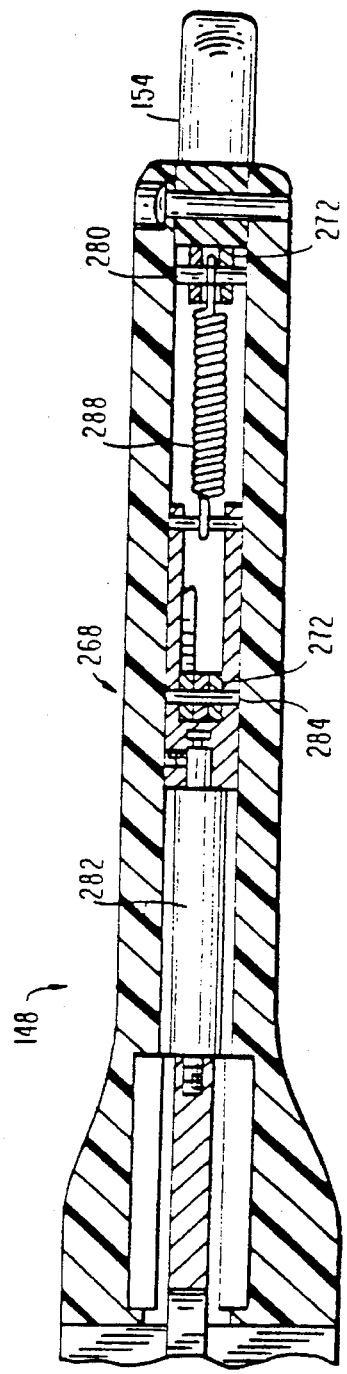

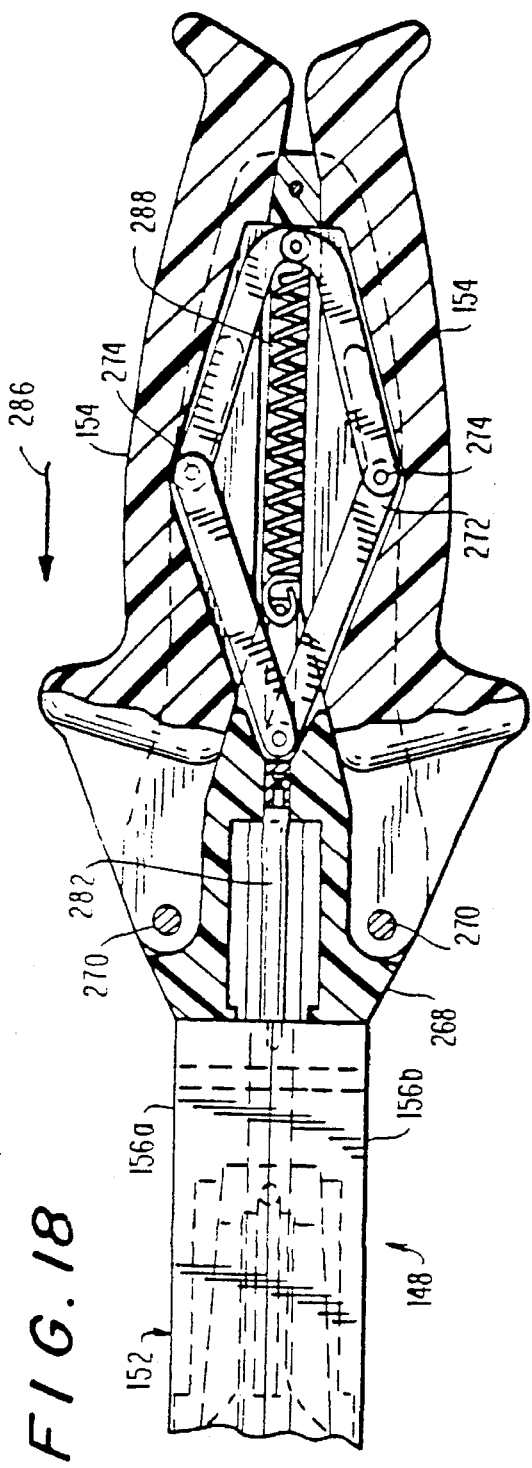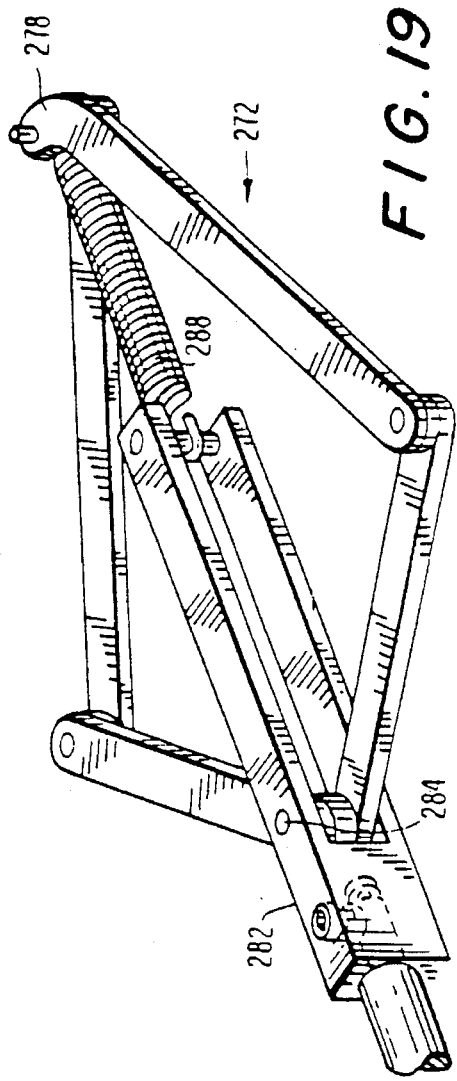

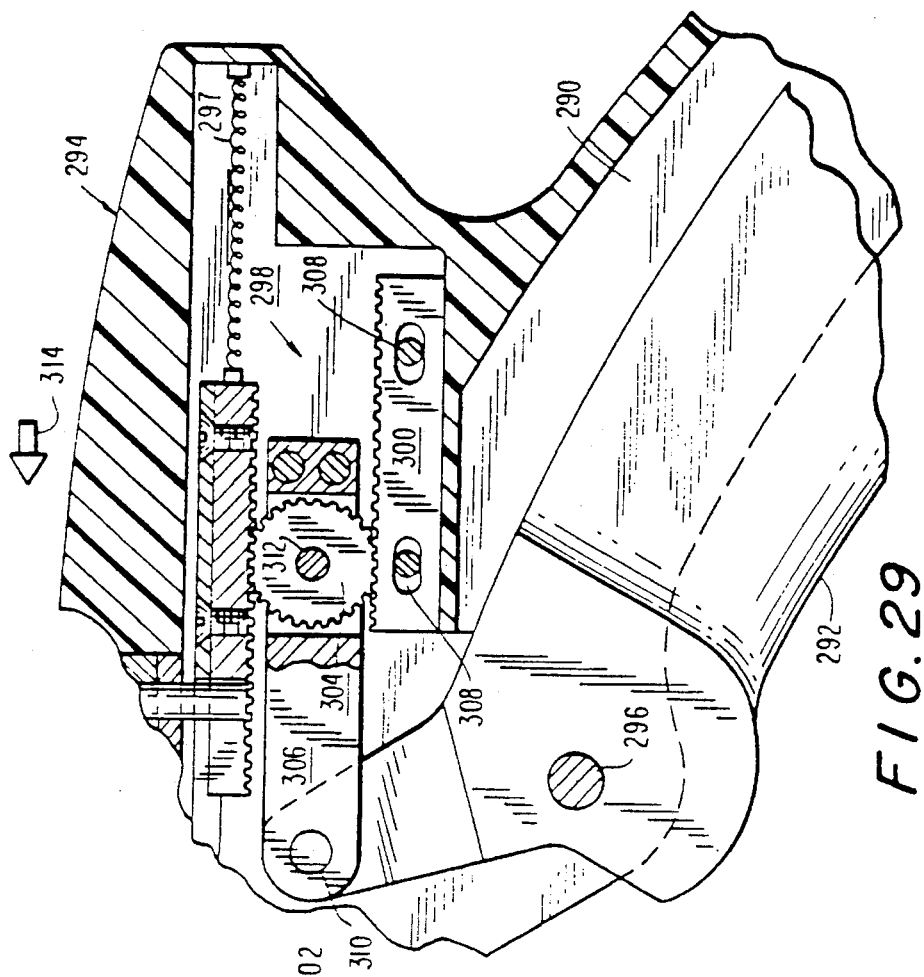
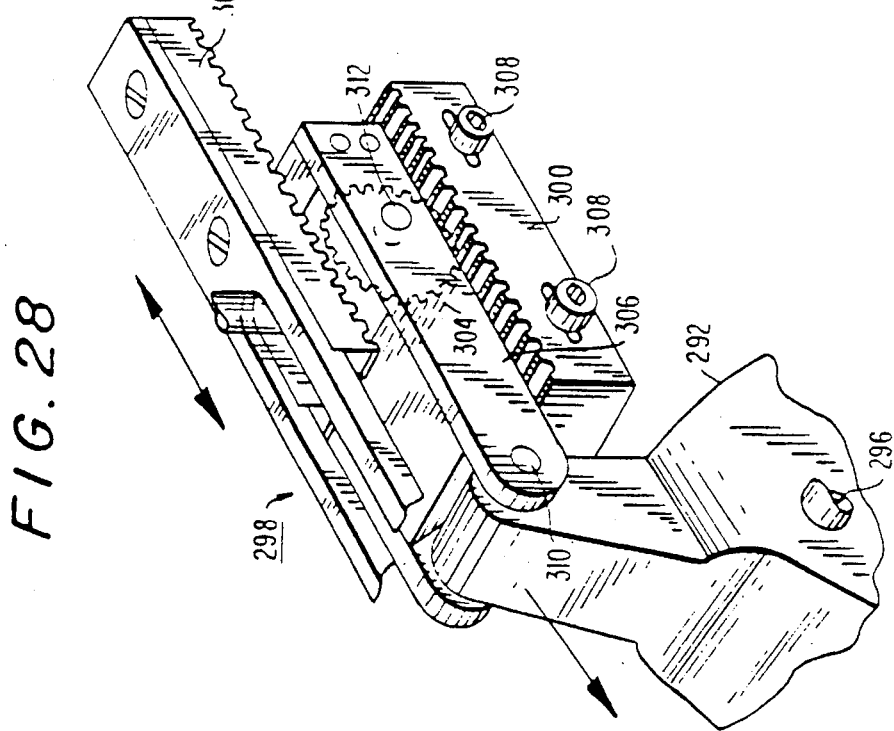
FIG. 29
FIG. 28

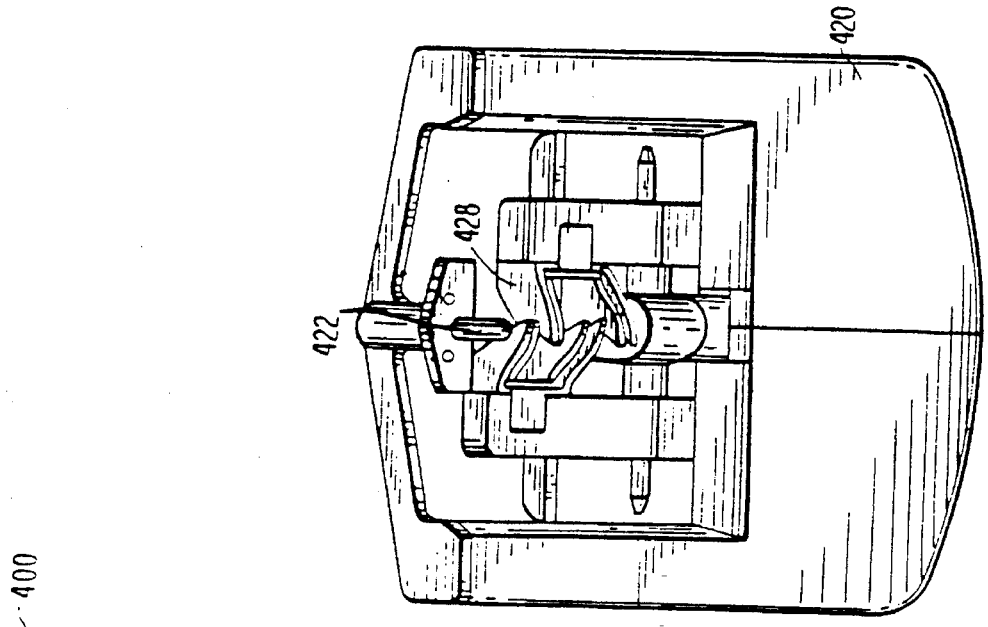
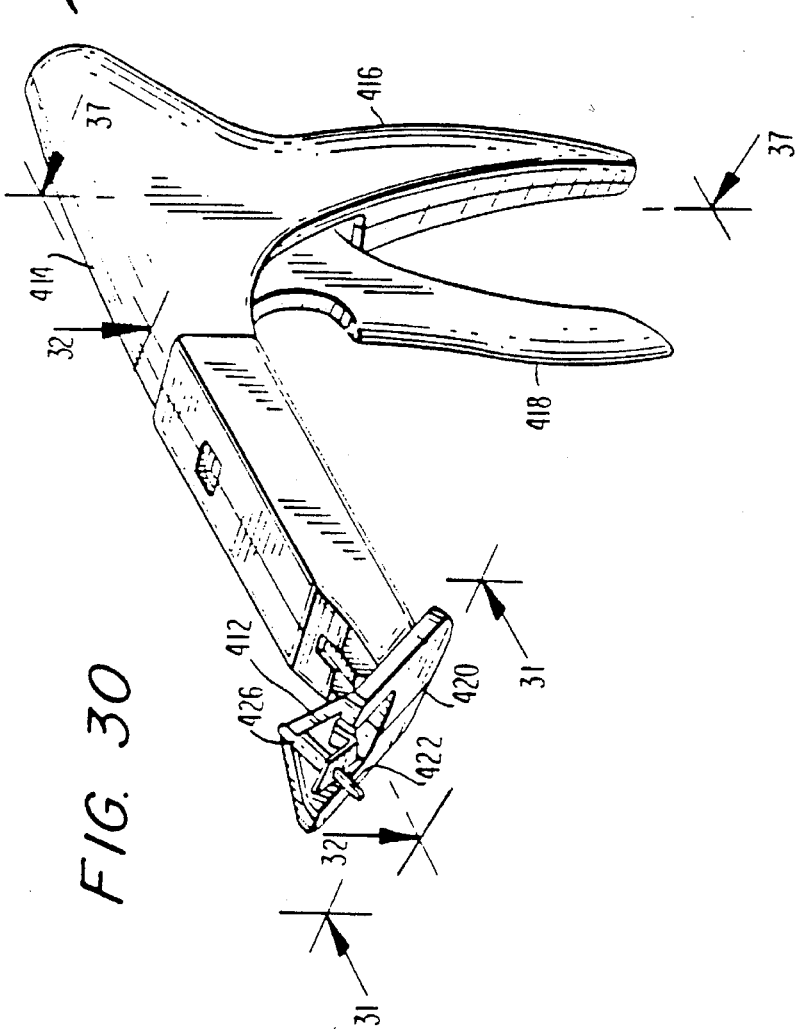
FIG. 30
FIG. 31

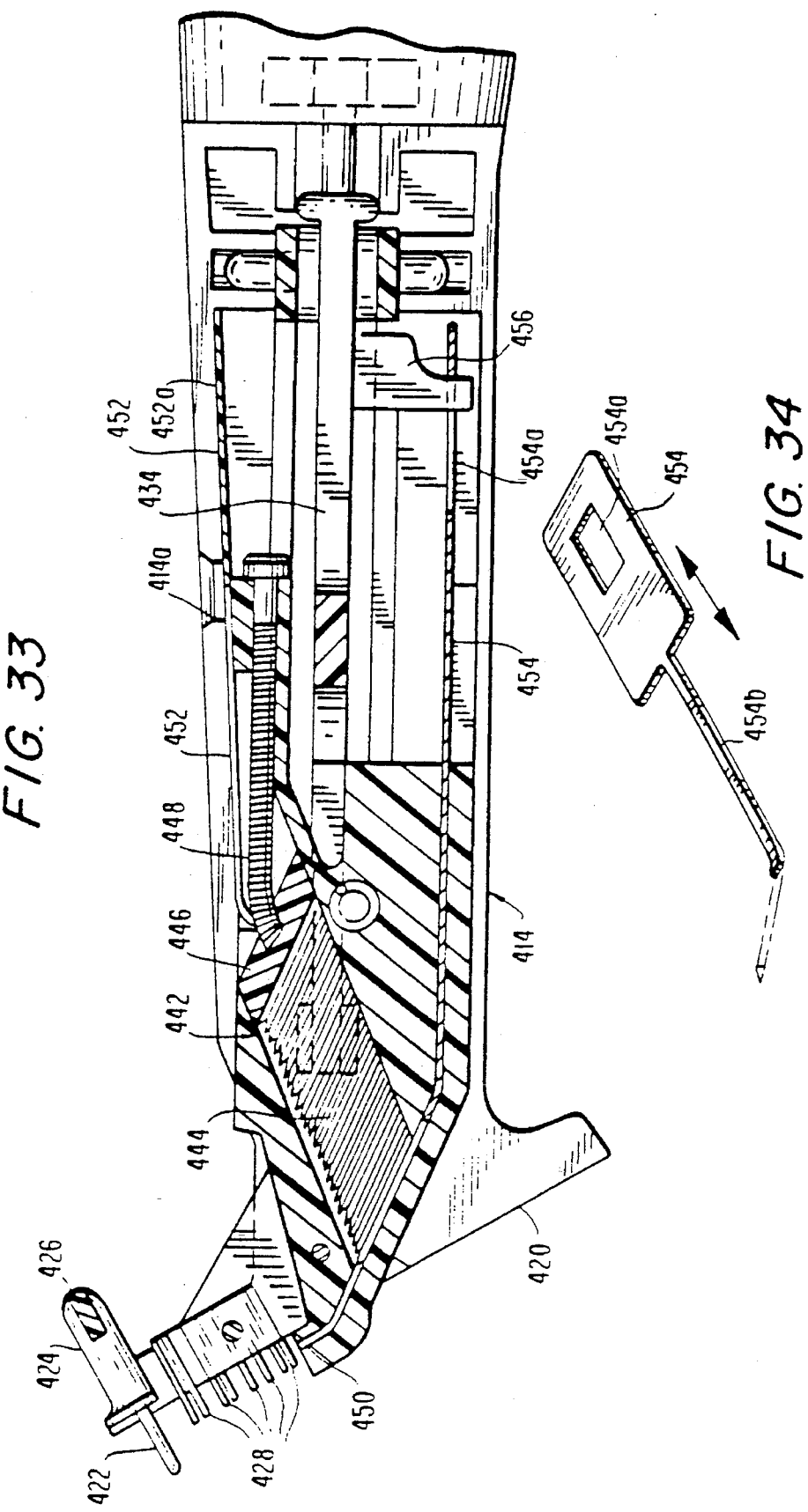

FIG. 40
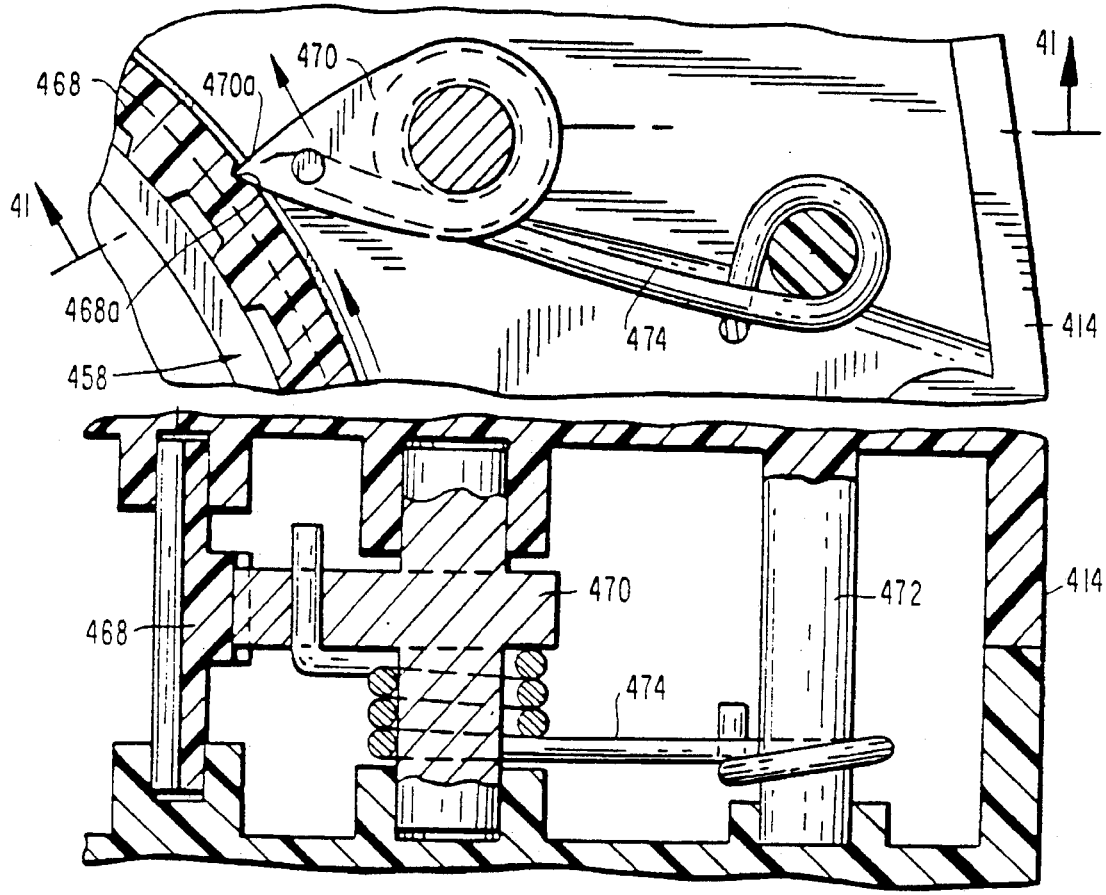
FIG. 41
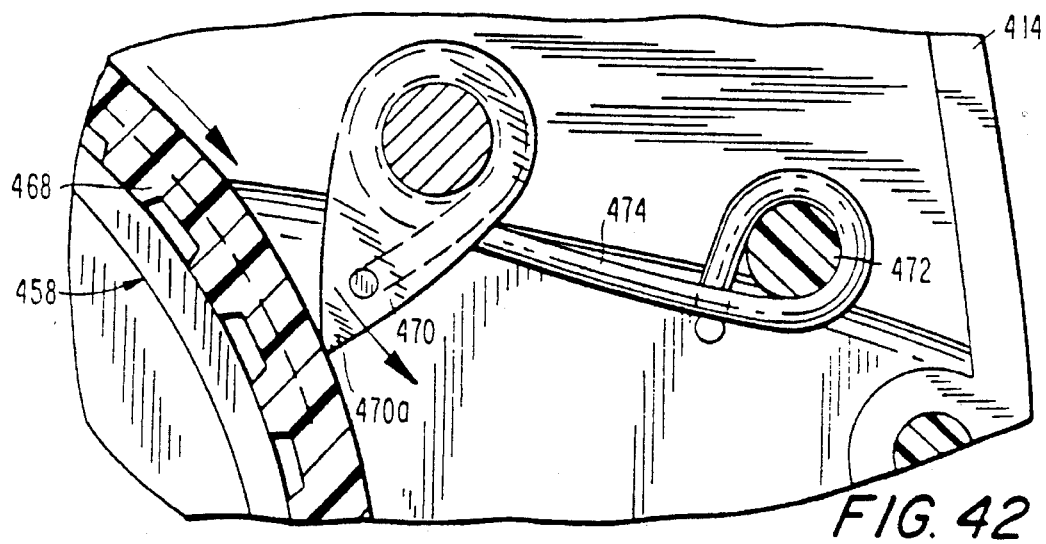
FIG. 42

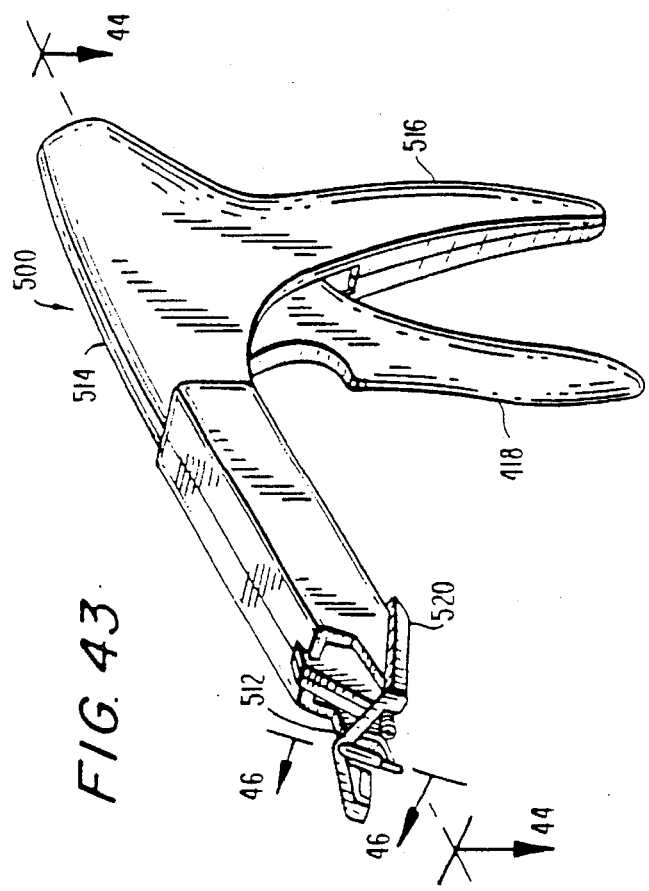
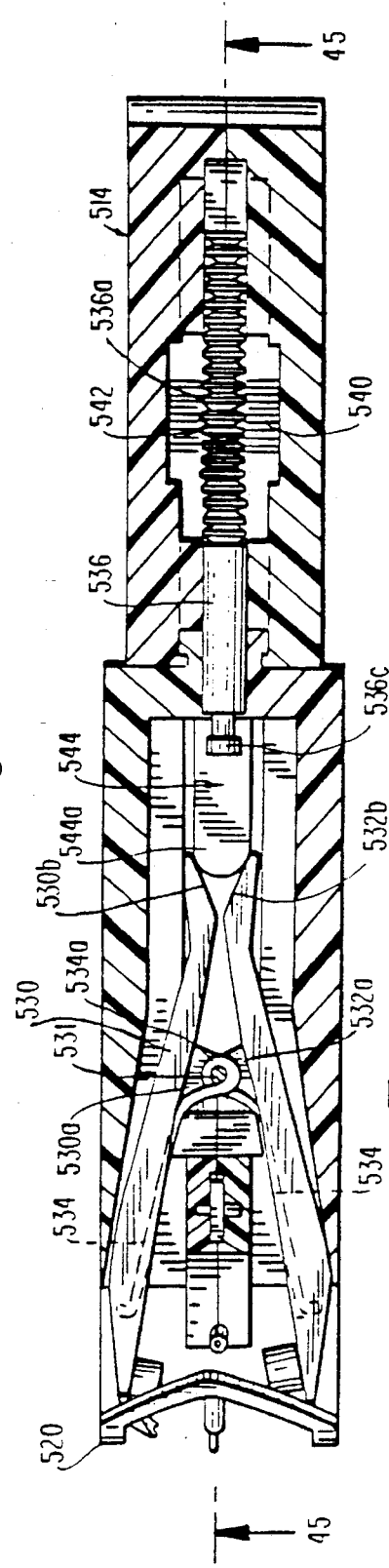
FIG. 43
FIG. 44

APPARATUS AND METHOD FOR SUBCUTICULAR STAPLING OF BODY TISSUE

CROSS REFERENCE. TO RELATED APPLICATION

This application is a divisional of U.S. application No. 07/959,242, filed Oct. 9, 1992, now U.S. Pat. No. 5,389,102, issued Feb. 14, 1995; which is a continuation-in-part of U.S. application No. 07/842,448, filed Feb. 27, 1992, now U.S. Pat. No. 5,292,326, issued Mar. 8, 1994; which is a continuation-in-part of U.S. application No. 07/630,224, filed Dec. 19, 1990, now abandoned; which is a continuation-in-part of U.S. application No. 07/581,776, filed Sep. 13, 1990, now abandoned.

BACKGROUND OF THE INVENTION

1. Field of the Invention

The present invention relates to an apparatus and method for subcuticular attachment of skin surrounding an opening wherein the opening is either caused unintentionally or by surgical procedure.

2. Discussion of the Prior Art

Modem day surgery using sutures and staples or the like is well defined. Generally, the key to successfully attaching cutaneous matter is the utmost gentleness in handling all tissue. Damaged and injured tissue leads to necrosis followed by fibrosis and scarring.

In handling tissue for attaching the surgical ends adjacent an opening, care must be taken in attaching the open ends to provide a minimum of the usual well-known telltale marks in the skin. For example, the application of sutures in cutaneous surgery will often result in the appearance of telltale crosshatch markings, whereas the use of sutures subcutaneously allows for early removal to minimize the telltale marks. Application of subcutaneous sutures generally refers to introduction of sutures at well below the epidermis and dermis. Subcuticular sutures generally refer to sutures introduced beneath the epidermis. In any event, reference to attachment of cutaneous matter below the epidermis at any level is sometimes referred to as "subcutaneous." Although the present description refers to subcuticular application of fasteners, it is contemplated that such fastener application can be performed at all levels possible with the application disclosed herein.

Surgically attaching cutaneous matter is also accomplished by application of staples which are generally of a metal material and are closed by action against an anvil which causes the ends of the staple to close after piercing the skin surrounding an opening. In either case, the portions of skin are first drawn together and then stapled or sutured so as to hold them together until natural healing takes place. The steps are often cumbersome to the surgeon since holding the skin together requires one motion and stapling or suturing requires another.

To date, there does not appear to exist an apparatus which is capable of gripping the portions of cutaneous matter surrounding an opening and drawing them together, followed by introduction of a staple at subcuticular levels, i.e. below the epidermis. Neither does there appear to exist an apparatus which is capable of drawing the cutaneous matter together and firing a staple in the subcutaneous region, i.e. in the region below the dermis. The present invention is directed to such an apparatus and method for attachment of cutaneous matter.

SUMMARY OF THE INVENTION

A surgical apparatus for attaching at least two adjacent end portions of a medium such as cutaneous body tissue which comprises a pair of jaws carried by a frame, means for moving the jaws toward and away from each other, and body tissue engaging means extending from each jaw and facing the opposed jaw and adapted to engage the respective opposed portions of the medium such that when the jaws are moved from a first open position toward each other to a second closed position, said engaging means causes the two end portions of the medium to be displaced toward each other, drawn together in close approximation, and to assume an irregular or undulating waveform shape whereby an elongated rod-like fastener may be directed generally medially of the medium to attach opposed portions of the medium.

Mechanical means is provided for moving the jaws toward and away from each other by actuation by manually gripping means manually movable toward each other to actuate the mechanical means.

Preferably, the means for moving the jaws toward and away from each other include a cam face on each of the jaws, and cam engaging means provided in the form of a fork that engages against the cam faces to move the jaws toward each other. The fork is slidably carried by the frame, with its tines positioned adjacent the cam faces, and is movable from a first position to a second position to engage its tines against the cam faces and move the opposed jaws towards each other to their closed position.

Included with the means for moving the jaws toward and away from each other is a pair of handles which, when squeezed toward each other, move the fork from its first position to its second position. As the handles are squeezed together, the pivotal motion of the handles is translated to longitudinal motion to move the fork from its first position to its second position.

Plunger means in the form of a plunger rod is provided which is movable from a first position to a second position to engage the elongated rod-like fastener to direct it generally medially of the interface and subcuticularly of the body tissue to thereby attach the end portions. The plunger rod is movable by movement of the fork as it moves from its second position to a third position as the handles are subsequently squeezed further together; the additional pivotal motion of the handles being translated to longitudinal motion to move the fork. When the handles are released, spring action returns the handles, fork and opposed jaws to their first position.

Preferably, each jaw includes a sharp pointed member positioned for engagement with marginal end portions of skin adjacent an opening therein such that when the jaws are displaced toward each other, the skin portions move toward each other and into engagement and assume an undulating waveform configuration at the interface therebetween. The apparatus further comprises a cartridge positioned adjacent the jaws and adapted to support a plurality of elongated rod-like fasteners, each having a sharp pointed tip at its proximal end to facilitate subcuticular penetration of the skin.

Each of the embodiments of the cartridge of the invention include means to resiliently bias the rod-like fasteners toward a position in which the fasteners can be advanced toward the body tissue when the body tissue is gripped by the sharp pointed members.

In an alternative embodiment a surgical apparatus is disclosed for attaching at least two portions of body tissue, which comprises, a pair of support members, a tissue gripping jaw supported at the distal end of each support member, body tissue engaging means extending from each jaw and facing the opposed jaw and adapted to engage respective opposed portions of the body tissue such that when the jaws are moved toward each other the engaging means causes the opposed portions of body tissue to be displaced toward each other and engage at the interface thereof so as to assume an irregular shape whereby an elongated fastener member may be directed generally medially of the body tissue interface to thereby attach the opposed portions of the body tissue. Resilient means is positioned between the support members to bias the support members and the jaws in opposed directions, and means is provided and configured and adapted for advancement in a distal direction in a manner to engage the support members whereby the support members and said jaws are caused to move toward each other. In this embodiment, actuating means is provided for engaging the pivotal support members so as to move the opposed jaws toward each other. The actuating means may comprise at least one handle manually movable to advance the actuating means.

The apparatus is particularly adapted to store and eject elongated rod-like fasteners and includes means associated with the rod-like fasteners to provide visual indication when a predetermined plurality of rod-like fasteners have been ejected. The indicator means may be in the form of a flag having a distinctively colored portion, i.e., yellow, or it may include appropriate calibration marks to indicate either the number of fasteners which have been ejected or the number of fasteners remaining.

In one embodiment a coil spring is incorporated to bias the pair of support members. Also, a strap or belt like member is attached to a manual gripping trigger and constrained to move along a curved path which converts the strap movement in a manner such that the distal end provides a distal force which is adapted through camming surfaces to cause the support members to pivot toward each other to close the jaws. A yoke having a central shaft having dual distally extending legs is provided with a roll being supported on each leg. Further, the belt or strap-like member may be a flexible metal strap and includes a pad of resilient material, such as nylon, which is arranged to pass a spring biased pawl. The pawl permits the belt to move freely over a curved path to provide distal closing and fastener spring force. However, within a predetermined portion of the distal movement of the belt the movement may be stopped to permit the surgeon to stabilize the position and orientation of the jaws without loss of the distal movement thus far achieved. This is accomplished by engagement of the pawl with the nylon pad.

The elongated fasteners are supported in a cartridge which may be either refillable or removable and replaceable. The fasteners are biased toward the firing position by a coil spring and they are ejected from the cartridge by an ejection plate which is arranged to sequence the fastener firing step after the jaws are closed.

A wide base stabilizer platform encompasses the jaws and provides a stable positioning means for stabilizing the position and orientation of the jaws for precise positioning of the fastener. The platform may be formed integral with the housing or support frame or it may be a separate detachable member.

In one embodiment distal jaw closing force and fastener firing force is provided by a rack type device which is a rod having a generally circular cross-section but which includes on the outer surface a plurality of individual teeth. The trigger, or manual actuating handle includes an arcuate shaped drive member which has a surface containing a plurality of teeth which mate with the teeth on the rack. When the trigger is squeezed toward the fixed hand grip, the teeth on the drive member engage the teeth on the rack and cause the rack to advance distally to provide the force required to approximate the jaws and to advance the fastener. An appropriate sequencing and fastener drive means such as the fastener drive plate disclosed herein may be incorporated. A system is provided in this embodiment to permit the operator to discontinue the distal motion on the rack by incorporating a leaf-type spring pawl arranged to engage an associated toothed surface over a predetermined range of movement of the trigger. Thus should the operator wish to stop the movement to facilitate stabilizing the position and orientation of the jaws to precisely position the fastener the movement can be stopped without loss of trigger position. After the orientation and positioning is perfected, the movement may be resumed. At the end of the stroke, the trigger is then permitted to return to its rest position by movement of the pawl spring out of interference with the toothed surface. A wire type pawl spring may also be used.

Staple storing means is provided in the form of a cartridge in which the rod-like fasteners are stacked and biased toward the ejecting position by a spring biased follower. The cartridge may be permanently attached to the apparatus or it may be removable and replaceable or refillable. A unique fastener drive plate is provided which is preferably in the form of a coil spring, the drive end of which is biased in the proximal direction. Distal force is provided by the trigger and associated rack to force the distal drive end of the spring forwardly to eject a fastener, after which it is permitted to return to the proximal position under its own spring force. Alternatively, a separate fastener drive plate may be attached to the distal end of the coil spring. Thus when the yoke is advanced distally a predetermined portion of the jaws are forced closed. Further distal movement of the yoke causes the drive member to engage the distal edge of the coil spring such that further movement of the member causes the fastener drive spring to move distally to engage the fastener next-in-line to eject it from the cartridge.

BRIEF DESCRIPTION OF THE DRAWINGS

Preferred embodiments of the invention are described hereinbelow wherein:

FIG. 1 is a left side perspective view from above, illustrating the improved apparatus for subcuticular or subcutaneous fastening of body tissue;

FIG. 2 is a partial cross-sectional view taken along lines 2—2 of FIG. 1;

FIG. 3 is a cross-sectional view with portions cut away, taken along lines 3—3 of FIG. 2;

FIG. 4 is a cross-sectional view taken along lines 4—4 of FIG. 3;

FIG. 5 is a cross-sectional view taken along lines 5—5 of FIG. 3;

FIG. 8 is a perspective view from above, of the pincer jaws of the apparatus in the closed position about an opening in body tissue;

FIG. 9 is a cross-sectional view from above, of the jaw closing mechanism of the apparatus of FIG. 1;

FIG. 10 is a cross-sectional view take along lines 10—10 of FIG. 9, illustrating a low profile system for storing a plurality of rod-like fastener members;

FIG. 11 is a view taken along lines 11—11 of FIG. 10, illustrating a rod-like fastening member positioned in body tissue to retain the tissue portions on each side of the opening in abutting relation;

FIG. 12 is a frontal view of the pincer-jaws of the apparatus of FIG. 10 and fastening member taken along lines 12—12 of FIG. 11;

FIG. 13 is a cross-sectional view of body tissue portions held by a subcutaneously positioned rod-like fastener member in adjacent engaged relation so as to promote healing;

FIG. 14A is a greatly enlarged perspective view with parts separated for convenience of illustration, showing the portion of the apparatus used for stacking and advancing rod-like fastener members for piercing body tissue;

FIG. 14B is a greatly enlarged perspective view of an alternate embodiment of the mechanism for advancing the fastener members;

FIG. 15 is a perspective view from above illustrating an alternative embodiment utilizing a scissor-type handle for actuating the pincer jaws and the fastener firing mechanism;

FIG. 16 is a partial cross-sectional view of the proximal handle portion of the apparatus of FIG. 15 taken along lines 16—16 of that FIG.;

FIG. 17 is a cross-sectional view taken along lines 17—17 of FIG. 16 illustrating the scissor-type actuating mechanism for closing the jaws and for advancing fastener members;

FIG. 18 is a view similar to FIG. 15 illustrating the manually operable handles in the closed position after firing the fastener member;

FIG. 19 is a greatly enlarged perspective view of the jaw closing and fastener advancing mechanism which forms part of the embodiment of FIG. 15;

FIG. 28 is a perspective view greatly enlarged, of the rack and pinion mechanism of the apparatus shown in FIG. 26;

FIG. 29 is a partial cross-sectional view of the rack and pinion section of the apparatus of FIG. 26 with the rack and pinion system in position corresponding to closed jaws after the fastener has been fired;

FIG. 30 is a perspective view from above of another alternative embodiment of the apparatus of the invention which incorporates additional features for subcuticular or subcutaneous stapling of skin;

FIG. 31 is a view taken along lines 31—31 illustrating an alternative arrangement of sharp skin gripping tips and a unique stabilizer platform;

FIG. 33 is an enlarged view partially in cross-section, taken along lines 33—33 of FIG. 32 illustrating the fastener biasing and firing mechanism of this embodiment;

FIG. 34 is a perspective view from above, of the mechanism for advancing the rod-like fasteners distally in the form of a fastener firing plate incorporated in this embodiment;

FIG. 40 is a view of the clutch system of the jaw closing and fastener firing mechanism of FIGS. 37–39 illustrating the positions of the pawl and resilient pad-type rack when the trigger is in the partially fired position with the ratchet mechanism in engagement;

FIG. 41 is a partial cross-sectional view taken along lines 41—41 of FIG. 40;

FIG. 42 is a view similar to FIG. 40 with the ratchet mechanism partially in the return position;

FIG. 43 is a perspective view of another alternative embodiment of the apparatus of the invention which incorporates an alternative mechanism for closing the jaws and firing the fasteners;

FIG. 44 is a view partially in cross-section, taken along lines 44—44 of FIG. 43 illustrating the jaw closing and fastener firing mechanism;

DETAILED DESCRIPTION OF THE PREFERRED EMBODIMENTS

Figure 6:
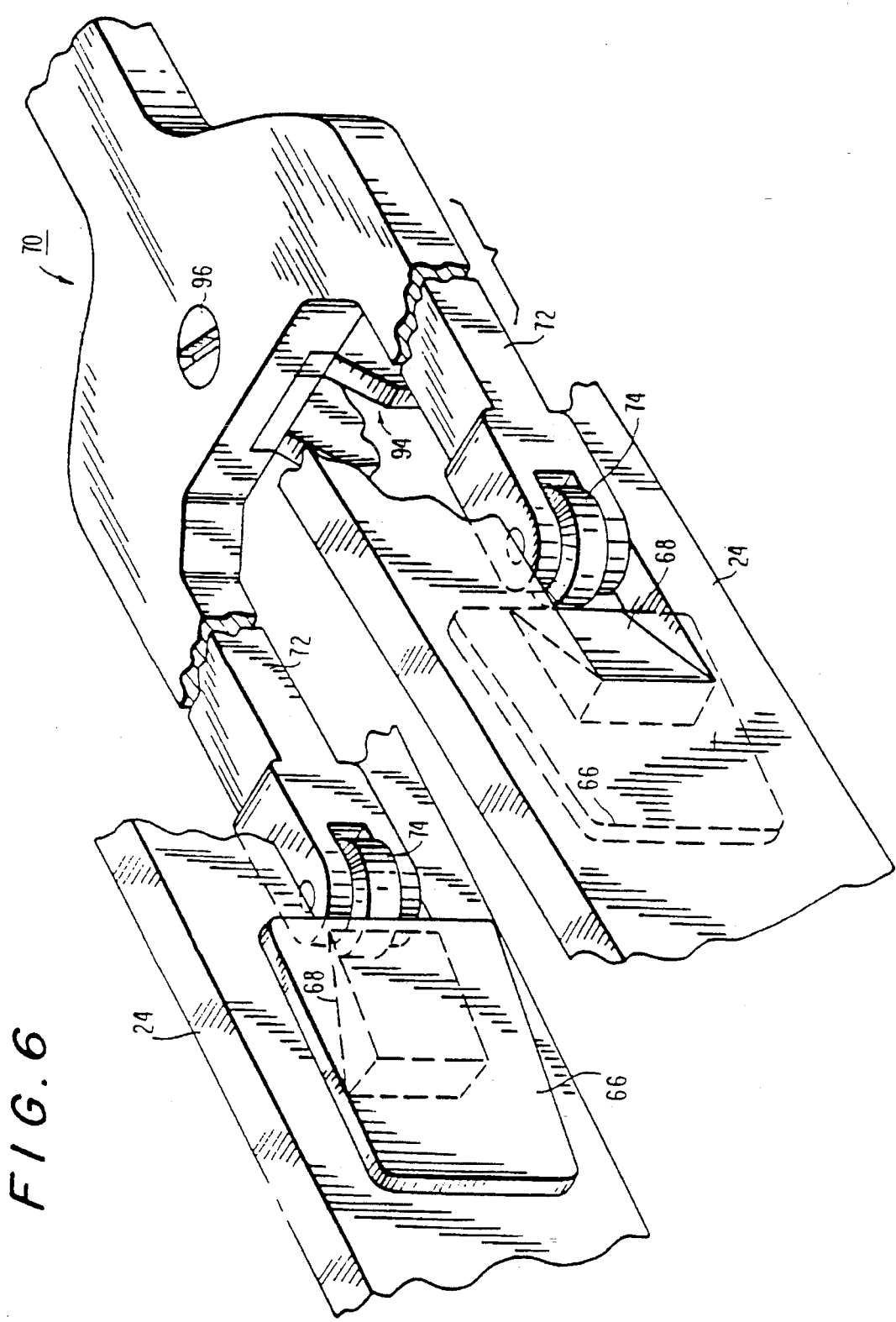
FIG. 6 is a greatly enlarged perspective view, of the cam and roller system for moving the pincer jaws of the apparatus toward and away from each other.

Referring initially to FIG. 1 there is illustrated generally an apparatus 10 for subcuticular or subcutaneous stapling of skin constructed according to the present invention. In general, the apparatus includes a pair of opposed jaws 12 movable from a spaced apart open position to a closed position to approximate tissue, a mechanism for camming the jaws to their closed position, and a mechanism for firing fasteners subcuticularly into the approximated tissue portions. A pair of handles 16, extending generally transversely from housing 14, operate to cam jaws 12 and to fire the fasteners in a manner which will be described hereinbelow.

Jaws 12, which extend from housing 14, are resiliently biased away from each other, and are movable between a normally open position as shown in FIG. 2 to a closed position as shown in FIG. 9. A guide shaft 13 extends slidably through the pair of opposed bores in jaws 12 to provide for accurate alignment of jaws 12 as they are moved between their open and closed positions.

Each jaw 12 includes a transverse gripping member 18 at its free end which is oriented generally at an obtuse angle with respect to its main portion. Transverse gripping members 18 are positioned opposite each other and extend generally toward one another, so that when jaws 12 are moved to their closed position, two portions of partially overlapping body tissue positioned between the gripping members 18 may be advanced into close approximation with each other.

Referring to FIG. 11, one gripping member 18a includes a U-shaped member 30 having a pair of spaced, sharp pointed skin gripping tips 28 with serrated ends which extend generally toward the opposite gripping member 18. U-shaped member 30 is removably attached to arm 24a by suitable means such as a screw 32. One end of the base of U-shaped member 30 may include a locator pin 34 positioned in a notch 36 in arm 24a to aid in restraining U-shaped member 30 from turning about screw 32.

The opposite gripping member 18b includes a pair of closely spaced, sharp pointed skin gripping tips 38 that are positioned medially between tips 28. As shown in FIG. 11, skin gripping tips 38 may similarly be provided in the form of a U-shaped member 40 having serrated tips at the ends of its closely spaced prongs, and removably attached to arm 24b by suitable means such as a screw 42. The base 44 of U-shaped member 40 may extend outwardly from prongs 46, laterally along arm 24b. One end of base 44 may include a locator pin 48 which is positioned in a notch 50 in arm 24b and aids in restraining U-shaped member 40 from twisting about screw 42.

Gripping member 18b may also include a third serrated skin gripping tip 52 in the form of an angularly oriented prong 54. Prong 54 is spaced from prongs 46 and is positioned so that its serrated skin gripping tip 52 is located outside tips 28. When jaws 12 are brought together as described in detail below, tips 28, 38, and 52 grip the portions of skin surrounding a body opening in a partially overlapping, sinusoidal waveform configuration as indicated by phantom line 56. Clearly, other configurations of prongs or a different number of prongs can be utilized to perform the function of approximating and holding the skin.

Referring to FIG. 2, housing 14 provides a frame for carrying jaws 12 and includes housing halves 19a, 19b, and removable cover 17 to allow ready access to the interior for ease of assembly. Elongated hollow 22 extends longitudinally into the end of housing 14 opposite handles 16. Each jaw 12 includes an elongated arm 24 extending generally longitudinally from hollow 22 with its transverse gripping members 18 positioned outside of housing 14. Arms 24 are pivotally interconnected inside the housing by a pin 26 for movement toward and away from each other and are of sufficient structural rigidity to retain their shape when jaws 12 are moved to their closed positions. Alternatively, jaws 12 and arms 24 may be formed integrally, interconnected at their enclosed ends by a transverse web.

With continued reference to FIG. 2, a longitudinal divider is positioned between arms 24 and connected thereto at its enclosed end by pin 26. Divider 58 bisects hollow 22 and extends outwardly from hollow 22, terminating at front stabilizer plate 20. A pair of arcuate leaf springs 60 are positioned symmetrically about divider 58. The innermost ends of springs 60 are attached to divider 58 by suitable means such as a rivet 62, shown in FIGS. 3 and 10. Leaf springs 60 bias outwardly so that their free ends bias against arms 24 of jaws 12 to normally urge jaws 12 to their open position. A longitudinal slot 64, shown in phantom, extends along each side of divider 58 to provide a recess into which leaf springs 60 may longitudinally recede as jaws 12 are moved to their closed position, as shown in FIG. 9.

As best shown in FIG. 3, the foot of housing 14 provides a rear stabilizer portion 21. Front stabilizer 20 and rear stabilizer 21 assist in stabilizing the position of the apparatus 10 during attachment of portions of body tissue as hereinafter described. Alignment pin 59, which may be retractable, extends downwardly from front stabilizer plate 20.

Referring now to FIG. 6, the mechanism for closing the jaws 12 will be described. Each arm 24 of jaw 12 includes a cam section 66 having a cam face 68 positioned at an acute angle to arm 24. Each cam section 66 can be formed of stainless steel or other suitable materials. Accordingly, preferably cam section 66 is provided in the form of an insert which is molded to arm 24. Alternately, cam section 66 and cam face 68 may be formed integrally with arms 24.

Fork 70, as shown in FIGS. 2 and 6, is carried by housing 14 and is adapted to come into contact with cam faces 68 to close the jaws. Fork 70 is longitudinally mounted in housing 14 within a slot provided in divider 58 (not shown in the Figs). Referring to FIG. 3, fork 70 includes a longitudinal slot 71 through which pin 26 extends. Fork 70 is located in hollow 22 with the ends of its tines 72 having rollers 74 which roll along cam faces 68 as best shown in FIG. 6. As an alternate to rollers 74, a flatter surface to frictionally engage cam faces 68 can be provided. As shown in FIGS. 2 and 9, rollers 74 contact opposed inner wall portions 76 defining hollow 22 during the longitudinal movement of fork 70 from a proximal (first) position, as best seen in FIGS. 2 and 3, to a distal (third) position, shown in FIGS. 9 and 10. During this movement, fork 70 assumes an intermediate (second) position in which rollers 74 engage against cam faces 68, moving arms 24 toward each other and biasing springs 60 laterally into slots 64, to move jaws 12 to their closed position, as shown in FIG. 9.

Referring to FIG. 10, further longitudinal movement of fork 70 to its distal position causes a flexible, elongated rod-like fastener 78 to be ejected into a path between closed jaws 12. Fastener 78 has a sharp penetration tip 79 at its forward or proximal end (see FIGS. 11 and 13) and is described in parent applications U.S. Ser. No. 581,776, filed on Sep. 13, 1990, and U.S. Ser. No. 630,224, filed on Dec. 19, 1990. Each of the fasteners 78 are of length sufficient to engage oppositely sloped skin portions as determined by the dimensions and relative spacing of the pointed tips. Each of the fasteners 58 may include means on the outer surface for improved retention in position within the body tissue.

Referring now to FIG. 12, each transverse gripping member 18a, 18b includes a notch 80 which is alignable with the opposing notch 80 when jaws 12 are moved to their closed position. As can be appreciated, notches 80 provide a longitudinal void 82 which is coincidental with the path of the fastener 78.

Turning now to the mechanism for firing the fasteners through longitudinal void 82 and into the approximated body tissue sections, ejection mechanism 83 shown generally in FIGS. 3, 10 and 14 is positioned adjacent jaws 12 and includes an elongated plunger 84, an inner elongated stationary tubular member 86, and an outer tubular member 88, which concentrically surrounds tubular member 86 and is adapted to move longitudinally therealong. Stationary tubular member 86 is secured within a bore 89 adjacent the lower end portion of divider 58 by a screw 91, and extends longitudinally into the lower portion of hollow 22. Referring to FIG. 14B, elongated plunger 84 comprises a flexible wire-like rod that extends longitudinally through stationary tubular member 86 and into tubular member 88 where it is secured at its proximal end by suitable means so that it moves longitudinally with tubular member 88. Plunger 84 is preferably made of a super elastic metal. One example of such metal is NITINOL brand metal available from Raychem Corporation, Menlo Park, Calif. Clearly, other resilient materials can be utilized. As will be appreciated in the illustrated embodiment, the cross-section of plunger 84, at least at its distal end, is approximately equal to the cross-section of rod-like fastener 78.

Outer tubular member 88 and connected plunger 84 is movable longitudinally between a proximal (retracted) position as shown in FIG. 3 coinciding with the proximal position of fork 70, and a distal position as shown in FIG. 10, coinciding with the distal position of fork 70 to discharge fastener 78. Alternatively, as shown in FIG. 14B, the plunger 84 can include a transverse tab 85 which rides in a channel formed by the two cartridge halves to restrain movement of the plunger 84. The tab may optionally be positioned at a central portion of the plunger 84.

Referring again to FIGS. 3 and 10, stop block 90 is secured at the free end of outer tubular member 88. Annular abutment 92 surrounds outer tubular member 88 and is located distally of stop block 90. Crosshead guide 94 extends laterally from fork 70, and is connected thereto by screw 96 shown in FIG. 14 such that it moves with fork 70. Crosshead guide 94 is provided with a bore in which outer tubular member 88 is slidably positioned and is located between stop block 90 and annular abutment 92. Crosshead guide 94 is longitudinally movable along tubular member 88 from a position which contacts stop block 90, coinciding with the proximal position of fork 70, to a position which abuts annular abutment 92, coinciding generally adjacent the conclusion of the movement of fork 70 to the intermediate position (compare FIGS. 3 and 10). Thus, outer tubular member 88 moves with fork 70 as it moves to its distal position. During the return movement of fork 70 to its proximal position, tubular member 88 and fork 70 move together to return plunger 84 to the proximal position until crosshead guide 94 abuts stop block 90.

As best shown in FIGS. 3 and 10, plunger 84 travels along non-linear path 100 which is defined by linear segments 100a, 100b and arcuate segment 100c terminating in a linear segment 100d. Segment 100d is axially aligned with longitudinal void 82. As shown in FIG. 14, path 100 is formed by cartridge body halves 102a, 102b. As will be appreciated, path 100 provides a means for altering the directional vector of the ejected rod-like fastener 78.

Referring now to FIGS. 3, 4 and 14, the cartridge for storing the fasteners will be described. Fastener cartridge 106 shown in FIG. 3 is adapted to retain a number of rod-like fasteners 78 for sequential ejection, one at a time, in end to end relationship to fasten the end portions of body tissue in an opening which is greater in length than the length of a single fastener 108. Fastener cartridge 106 is configured to allow diagonal stacking of the fasteners to reduce the profile of the distal portion of the apparatus to increase the visibility of the user during Operative procedures. This diagonal stacking also increases the number of fasteners which can be stored in the apparatus. The cartridge may optionally be removably mounted in the apparatus to allow removal and replacement with another loaded cartridge.

The casing of fastener cartridge 106 includes body halves 102a, 102b which are attached together by suitable means. As shown, body half 102b may be formed integrally with divider 58, extending forwardly at the front end therefrom toward transverse gripping members 18.

Each body half 102a, 102b includes an elongated chamber portion 105a, 105b which cooperate when body halves 102a, 102b are assembled together to provide a chamber 105 in which fasteners 108 are stacked laterally in face-to-face contacting relationship along their respective longitudinal surfaces. The cross-sectional dimension of chamber 105 is equal to or slightly greater than the major diameter of;each rod-like fastener 108 to facilitate a snug fit, with the angular longitudinal length of chamber 105 being dimensioned to accommodate a predetermined number of fasteners 108. Chamber 105 extends rearwardly at an acute angle, thus allowing fasteners 108 to be stacked in diagonal fashion, in a cascading, partially overlapping lateral arrangement which ascends rearwardly as shown. This arrangement advantageously conserves space as compared to vertical stacking.

As shown in FIG. 4, fasteners 108 are biased downwardly in chamber 105 toward the firing chamber segment which extends between segments 100a, 100b. The bottommost fastener 78 is biased into the firing chamber segment where it is retained for ejection as its distal end 104 is adjacent operative end 103 of plunger 84. After each fastener 78 is ejected and discharged, plunger 84 is withdrawn longitudinally to its retracted position with the end 103 of plunger 84 returning to segment 100a, to allow the next fastener 78 to be biased downwardly into the firing chamber segment into a position suitable for egress from the fastener stack.

More particularly, as shown in FIG. 14, a pair of negator springs 110 act on transverse shaft 124 of follower 112 to bias fasteners 78 downwardly. Each negator spring 110 is positioned within a jacket 114 as shown, with its lower end secured within an arcuate slot 116 formed therein and its other end secured to a circular bushing 118. Each negator spring 110 in its initial position is partially unwound, the spring being resiliently biased toward a normal spiral configuration. As follower 112 slides downwardly in the chamber 105, the spring winds towards its spiral configuration. Follower 112 is positioned in chamber 105 adjacent the topmost member 120 of the stacked rod-like fasteners 78. Furthermore, a longitudinal slot 122 bisects each chamber portion 105a, 105b as shown and receives and holds one end of transverse shaft 124 of follower 112 as it moves downwardly in chamber 105 towards the firing chamber segment. The ends of shaft 124 are also held within the bore portions of bushings 118. Each jacket 114 may be provided with an elongated window 126 through which the position of follower shaft 124 may be visually observed to indicate the remaining number of rod-like fasteners 108 which are available.

Figure 7:
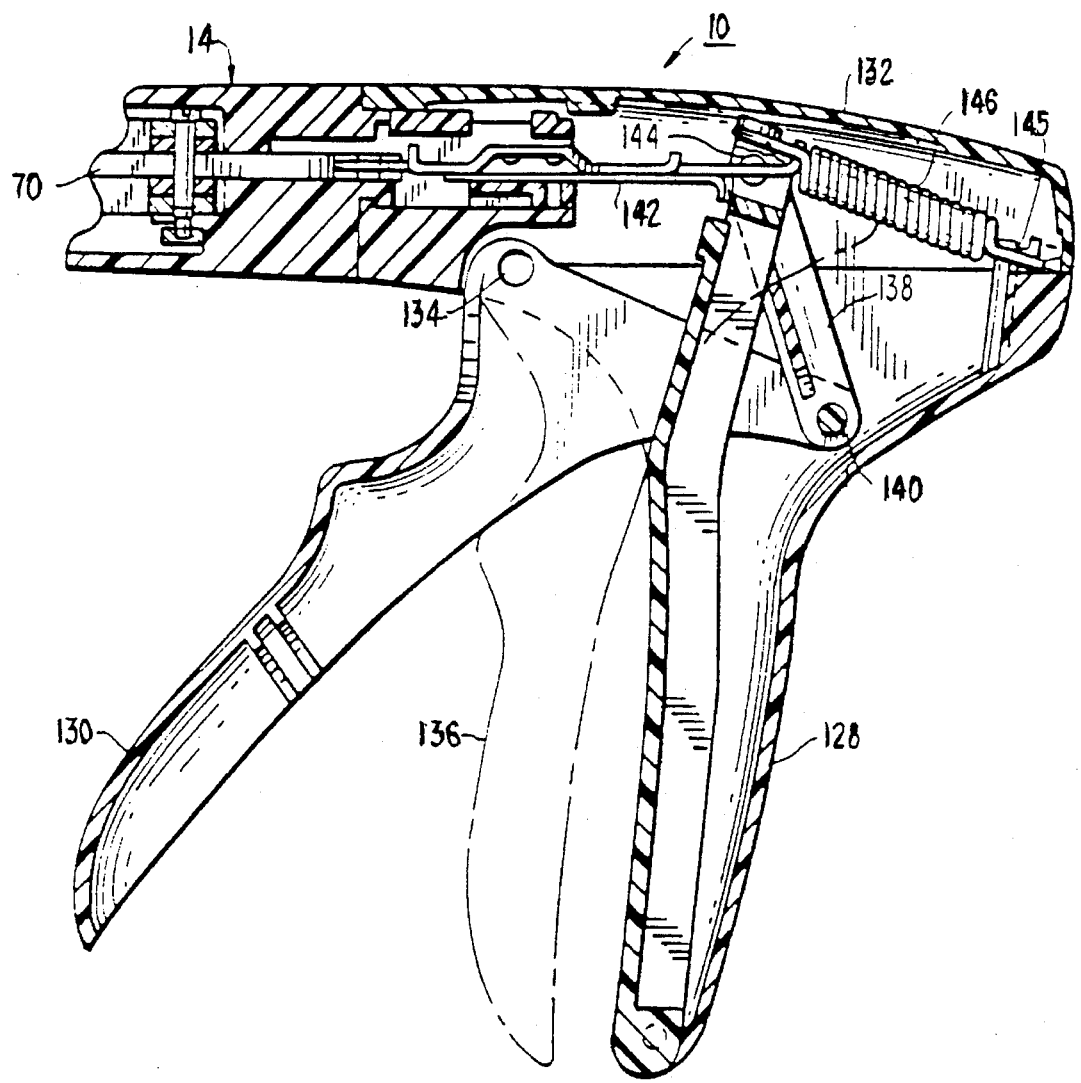
FIG. 7 is a cross-sectional view taken along lines 7—7 of FIG. 1, illustrating the proximal portion of one embodiment of the jaw closing mechanism.

Referring now to FIG. 7, a preferred mechanism for closing the jaws and for actuating plunger 84 is illustrated and includes handles 128, 130 extending generally transversely from housing portion 132. Handle 128 is formed integrally with housing portion 132 and handle 130 is pivotally connected via pin 134 to housing portion 132 for movement between an open position and closed position, as indicated by phantom lines 136 in FIG. 7. Squeezing of handle 130 toward handle 128 moves fork 70 from its proximal position to its distal position to thereby close jaws 12 and move plunger 84 longitudinally to discharge fastener 78 as will be described in more detail below.

A link member 138, pivotally connected via pin 140 to handle 130, translates the pivotal motion of handle 130 to longitudinal motion which moves fork 70 longitudinally distally. More specifically, link member 138 is pivotally connected via pin 144 to the rear end of drawbar 142, and drawbar 142 is connected at its distal end to the proximal end of fork 70. A spring 146 is attached to the proximal end of drawbar 142 and to housing portion 132, to cause drawbar 142 to move proximally when handles 128, 130 are released, thus returning fork 70 to its proximal position. Movement of drawbar 142 rearwardly also returns handles 128, 130 to their open position.

In operation, handles 130, 128 are initially squeezed together to move fork 70 distally such that rollers 74 engage cam faces 68 to force the jaws toward each other to bring the tissue portion into overlapping relationship and into an undulating configuration. Further squeezing of handles 128, 130 causes plunger 84 to move from its retracted position toward its discharge position so that its operative end 103 engages the lowermost fastener 78, positioned between segments 100a, 100b, causing it to be ejected (i.e. fired) distally into segment 100b. Continued movement of plunger 84 by fork 70 causes fastener 78 to move forwardly through arcuate segment 100c and to segment 100d where fastener 78 is discharged to penetrate the end portions of body tissue to attach the and portions together.

FIG. 15 illustrates generally another embodiment of the apparatus of the present invention, having a scissor-type handle mechanism. Apparatus 148 includes a pair of opposed jaws 150, similar to opposed jaws 12 in FIG. 1, extending from the distal end of housing 152 which encloses the jaw closing mechanism. A pair of handles 154 extend generally proximally from the proximal end of housing 152. Jaws 150 are resiliently biased away from each other, and are movable from their normally open position toward each other to a second closed position by squeezing handles 154 together. A guide shaft 155 similar to guide shaft 13 of FIG. 1 extends slidably through a pair of opposed bores in jaws 150 to restrain twisting of jaws 150 as jaws 150 are moved between their open and closed positions. Housing 152 may further comprise housing halves 156a, 156b, as shown, for ease of assembly.

Each jaw 150 includes transverse gripping members 158, similar to the transverse gripping members 18 shown in FIG. 1, oriented generally at an appropriate obtuse angle with respect to the main portion of the respective jaw 150. Accordingly, reference is made to the previous description in connection with FIG. 11 in conjunction with the gripping members 158 shown in FIG. 15. When jaws 150 are moved toward each other to a closed position, the two portions of partially overlapping bodily tissue positioned between gripping members 158 are brought into close approximation. Further movement of handles 154 toward each other causes thin elongated rod-like fastener 220, described above, to be discharged between gripping members 158 to penetrate the body tissue portions and attach the two body tissue portions together as described previously.

Figure 21:
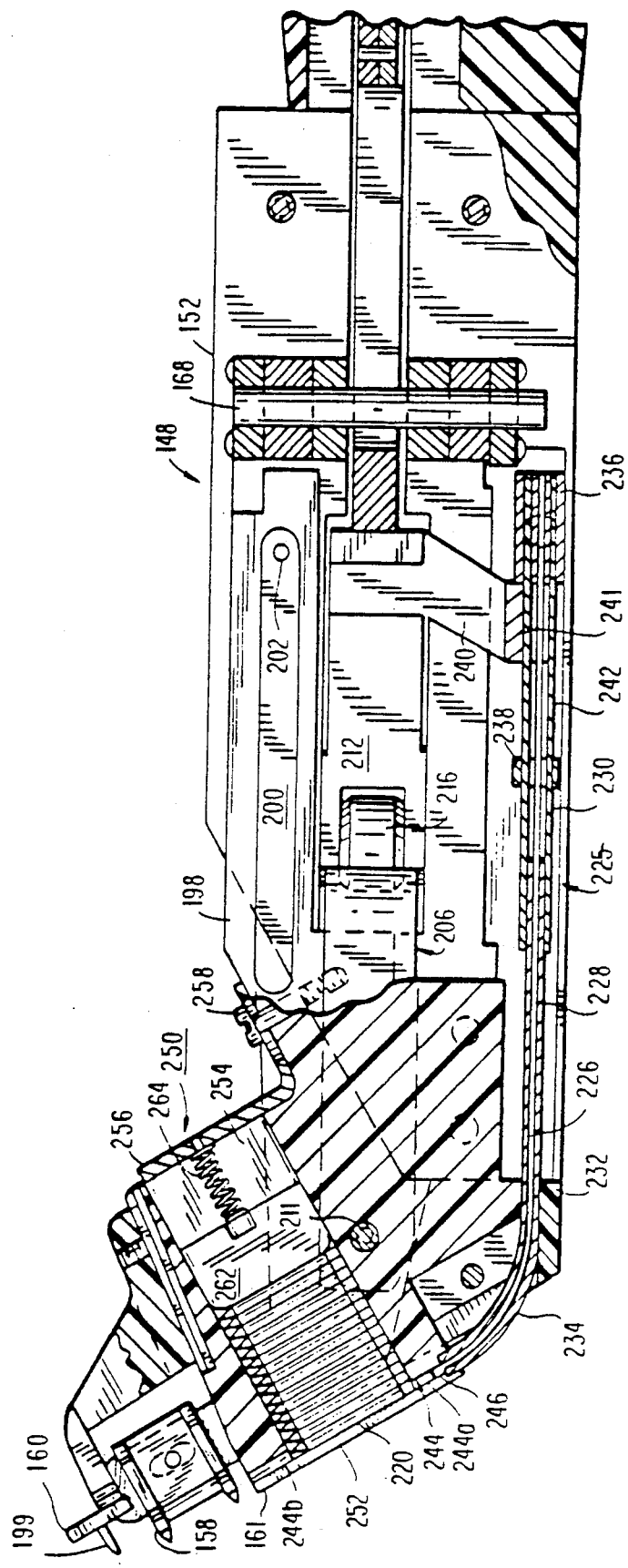
FIG. 21 is a cross-sectional view of the distal section of the apparatus shown in FIG. 15 illustrating an alternative type of fastener storing cartridge.
Figure 25:
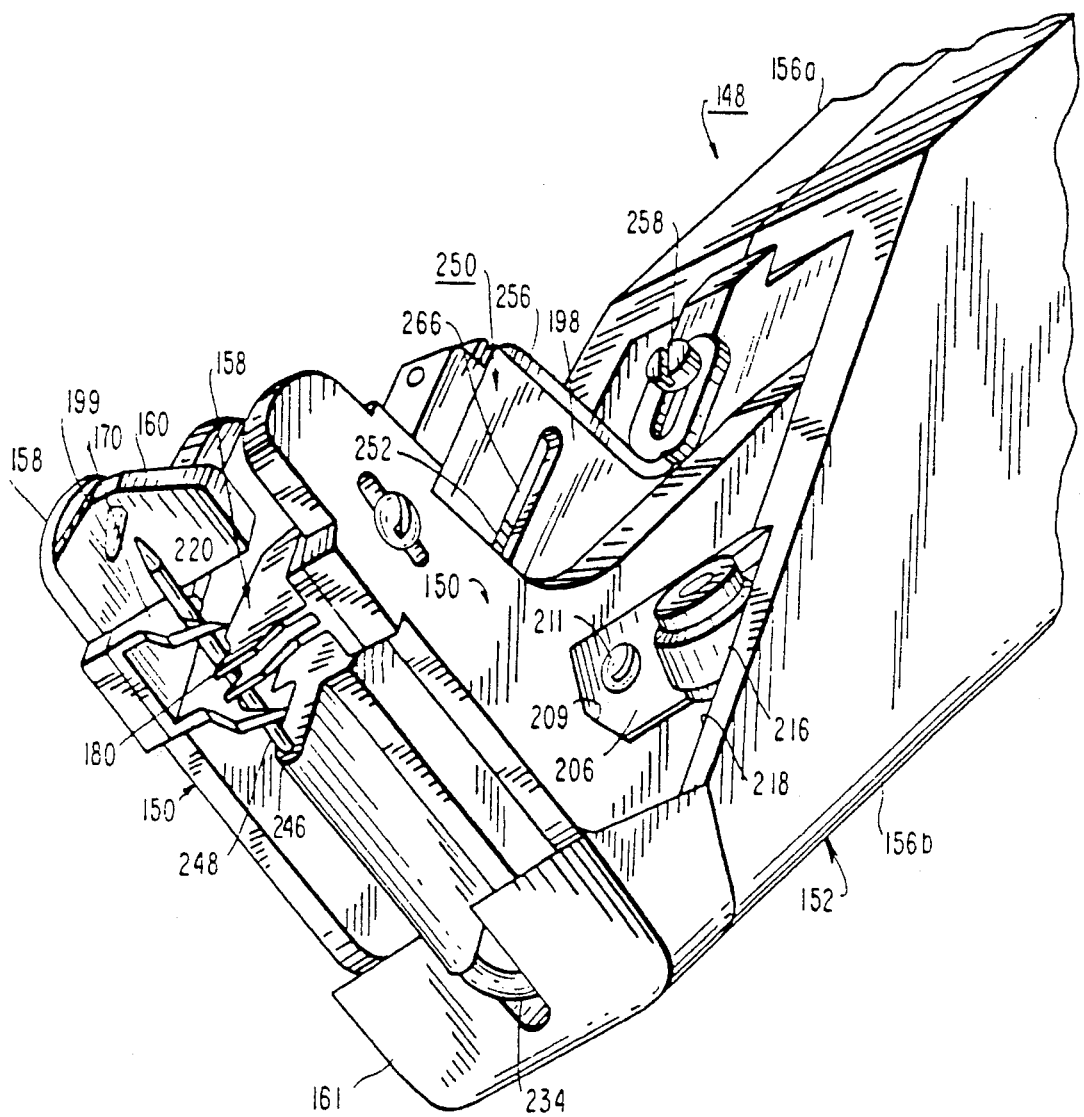
FIG. 25 is a view from below of the pincer jaws of the apparatus of FIG. 15 in the closed position during actuation of the fastener firing mechanism.

Referring to FIGS. 21 and 25, front stabilizer portion 160 includes an alignment pin 199, preferably retractable; extending downwardly therefrom. The foot of housing 152 provides a proximal stabilizer portion 161. Stabilizers 160 and 161 assist in stabilizing apparatus 148 during attachment of portions of body tissue as described below.

Figure 20:
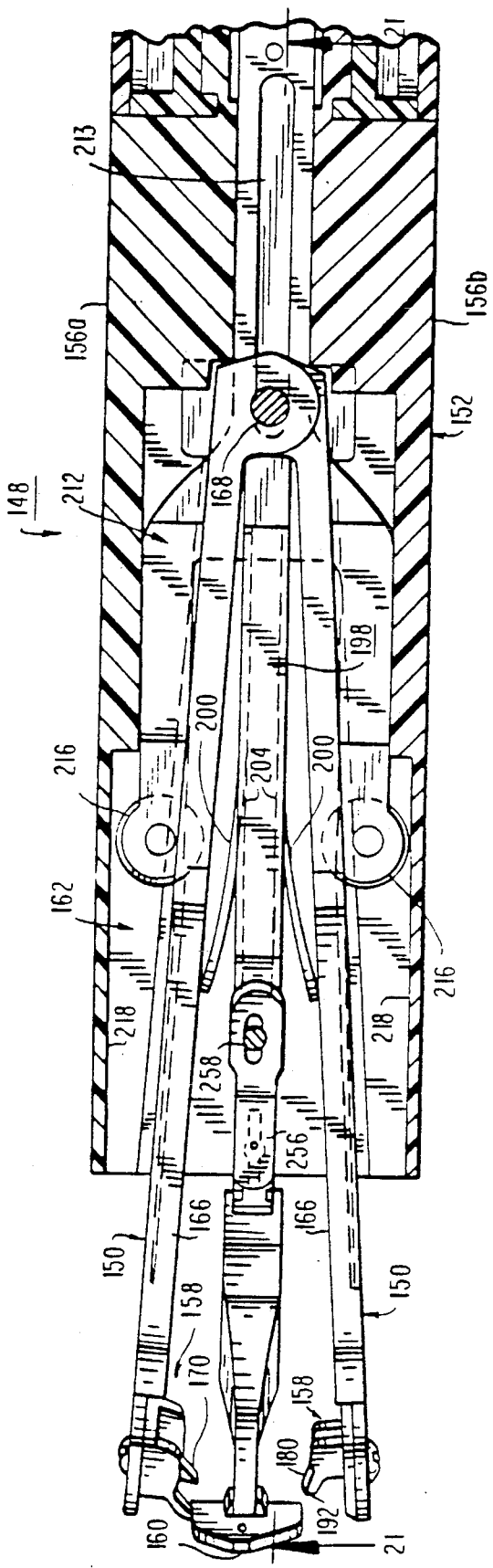
FIG. 20 is a cross-sectional view of the apparatus of FIG. 15 illustrating the roller-cam mechanism for closing and opening the pincer jaws.

Referring to FIG. 20, housing 152 provides a frame for carrying jaws 150. Jaws 150 extend into hollow 162 of housing 152 similar to the previous embodiment. Each jaw 150 includes an elongated arm 166 extending generally longitudinally from hollow 162 with its transverse gripping members 158 positioned outside of housing 152. Arms 166 are pivotally interconnected at their proximal ends by a pin 168 for movement toward and away from each other. Alternately, jaws 150 and arms 166 may be formed integrally, interconnected at their enclosed ends by a transverse web.

As in the first embodiment described above, a longitudinal divider 198 bisects hollow 162 and terminates at stabilizer plate 160. A pair of arcuate leaf springs 200 are attached to divider 198 by a rivet 202, shown in FIGS. 21 and 24, and bias jaws 150 to their open position. Longitudinal slots 204 provide a recess to receive leaf springs 200 when jaws 150 are moved to their closed position, as shown in FIG. 23.

Figure 22:
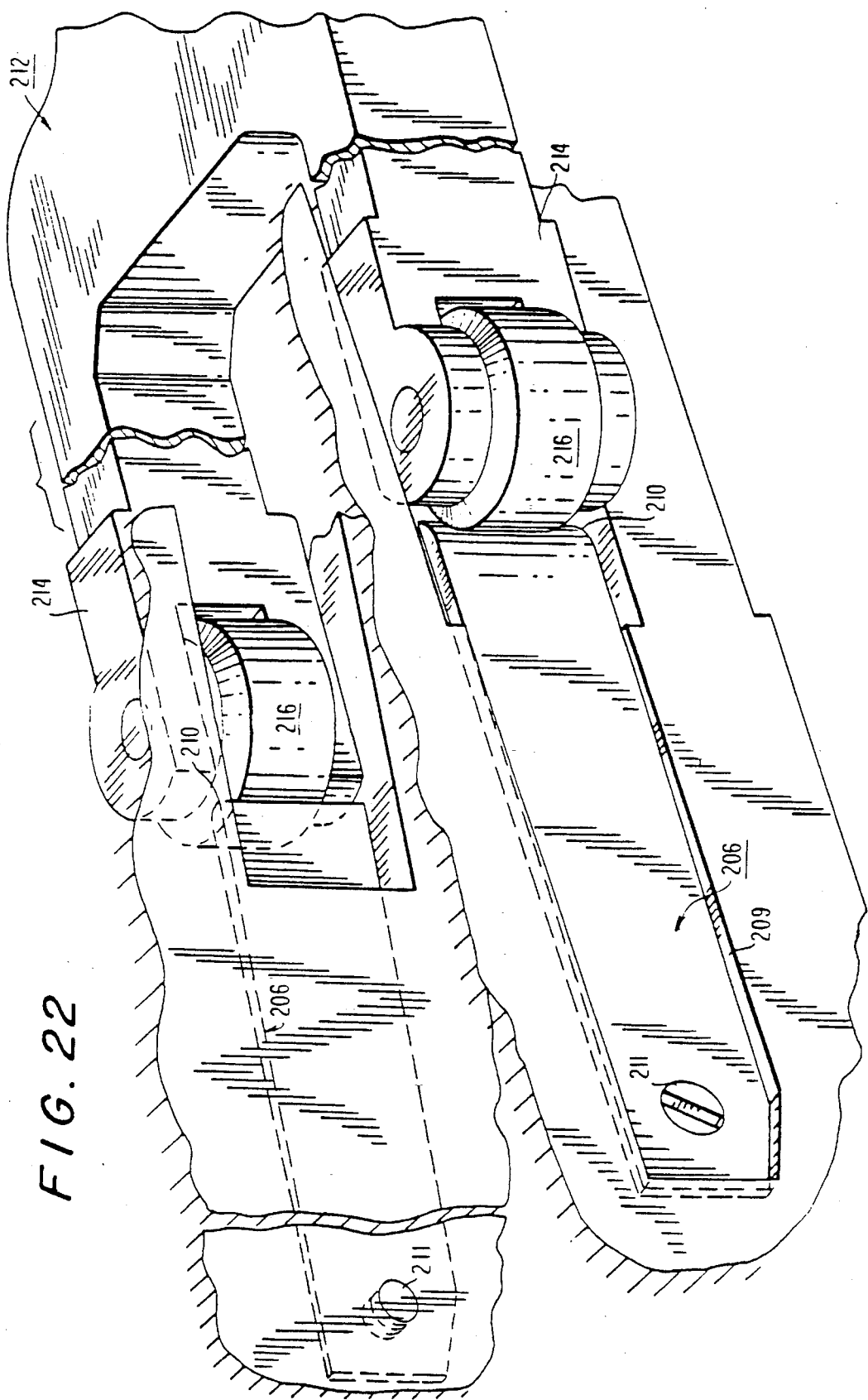
FIG. 22 is a greatly enlarged view from above illustrating the roller cam for closing and opening the pincer jaws of the apparatus of FIG. 15.

Referring to FIG. 22, each arm 166 includes a cam member 206 positioned along its outer face 208 and retained within a slot 209 in arm 166 by screw 211. Each cam member 206 includes a rearward facing beveled edge 210.

Figure 23:
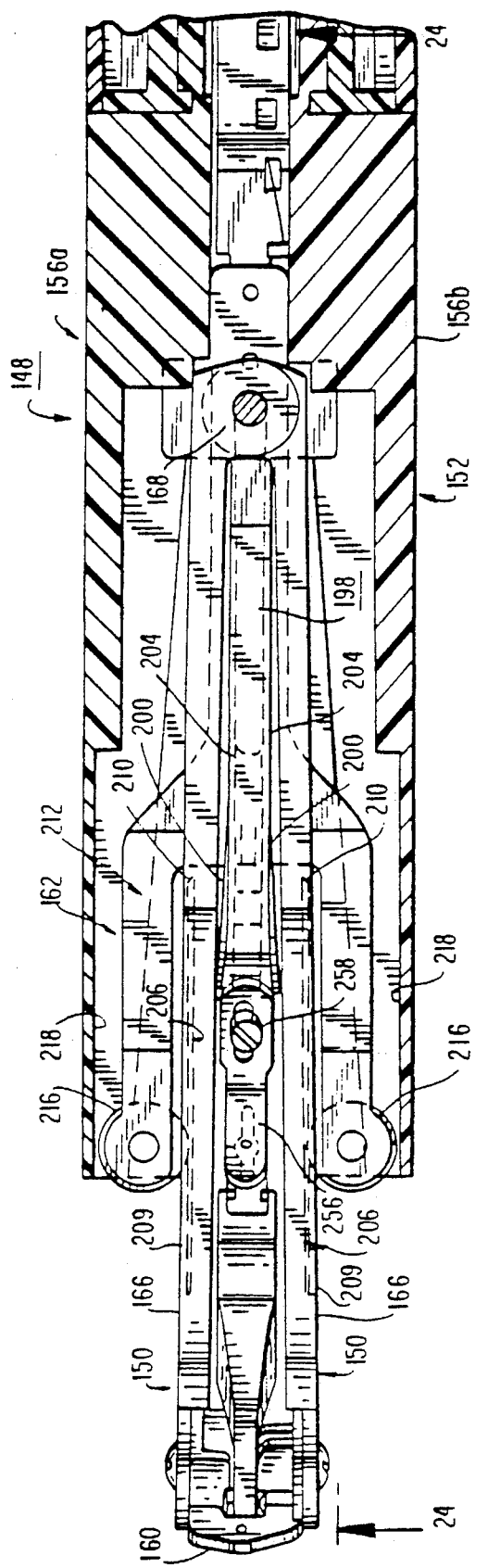
FIG. 23 is a cross-sectional view similar to the view shown in FIG. 20 with the pincer jaws in the closed position.

Fork 212, carried by housing 152, is similar to fork 70 in that it includes a longitudinal slot 213 through which pin 168 extends and has rollers 216 at the end of each tine to roll along and engage cam member 206 when moved from a proximal position, as best seen in FIGS. 20, to a distal position, shown in FIG. 23. Rollers 216 are positioned in elongated slots 218 in the interior wall of housing 152 to prevent twisting of fork 212 within hollow 162. Rollers 216 contact the opposed recessed wall portions of slots 218, and roll along recessed wall portions of slots 218 during the longitudinal movement of fork 212. The movement of fork 212 between its proximal position, intermediate position, and distal position for firing the fastener 220 is identical to the previous embodiment described with reference to FIGS. 2 and 6.

Figure 24:
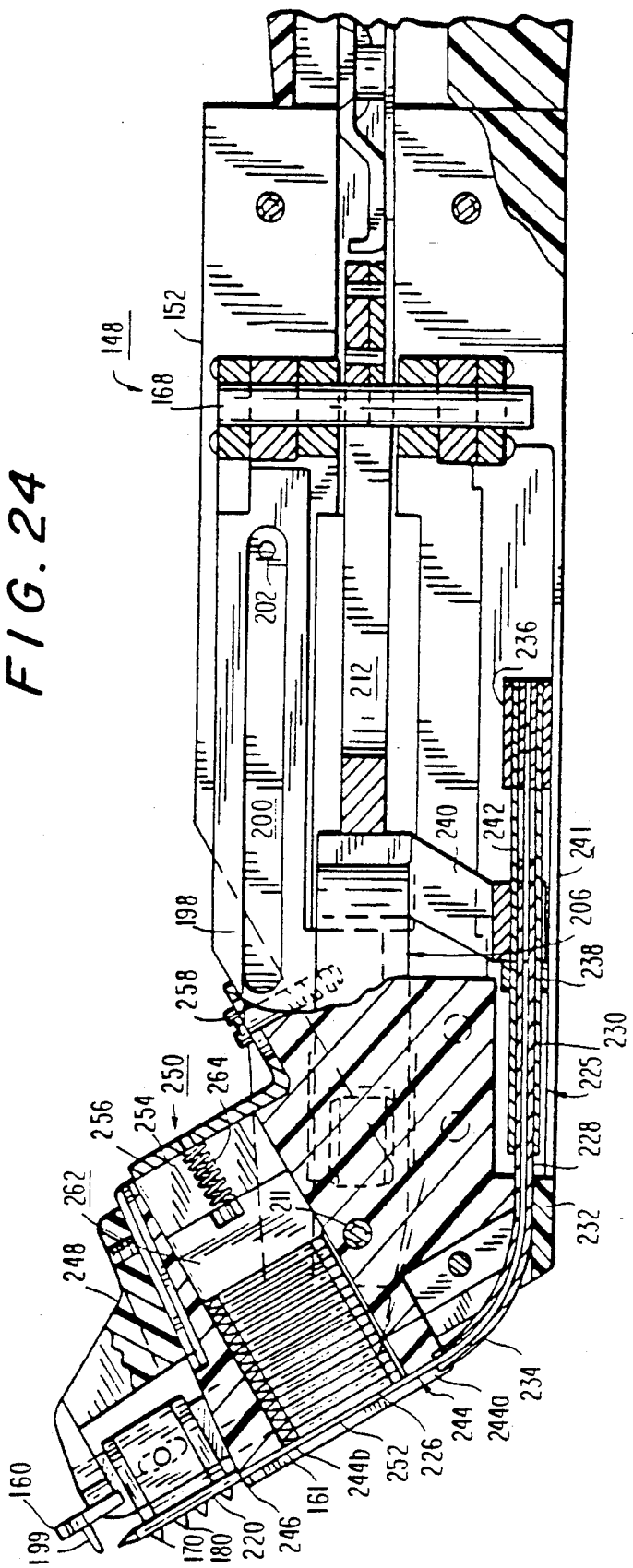
FIG. 24 is a cross-sectional view similar to the view shown in FIG. 21 with the firing mechanism advanced for firing a fastener.

The mechanism 225 (FIG. 21) for ejecting fasteners 220 are similar to that described with respect to the first embodiment. The mechanism includes an elongated plunger 226, an inner, elongated stationary tubular member 228 and a longitudinally movable outer tubular member 230, which concentrically surrounds tubular member 228 and is adapted to move longitudinally therealong. Referring to FIGS. 21 and 24, tubular member 228 is secured within a bore 232 and includes an arcuate, curved portion 234. Plunger 226 comprises a flexible wire-like rod, preferably composed of the same material as plunger 84, that extends longitudinally through stationary tubular member 228 into tubular member 230. As may be appreciated, the cross-section of the wire-like rod approximately matches the cross-section of fastener 220. The enclosed end of plunger 226 is secured within tubular member 230 such that plunger 226 moves longitudinally with tubular member 230.

In operation, the mechanism for approximating the body tissue and for firing the rod-like fasteners is identical to the operation described for the embodiment shown in FIGS. 2–6. However, the actual rod-like firing system is unique in some respects to the embodiment of FIG. 15 as is described below.

Referring once again to FIG. 21, path 244 comprises a pair of spaced, axially aligned segments 244a, 244b, with segment 244a connecting with arcuate, curved portion 234 of tubular member 228, and segment 244b connecting with longitudinal void 224 formed between the closed jaws. Path 244 is similarly provided by furnishing the cartridge body extension of divider 198, hereinafter described, with bore-like passages constructed as previously described.

Prior to ejection, fastener 220 is axially aligned between segments 244a, 244b and plunger 226 and is positioned in segment 224a with its proximal end 246 abutting the distal end 248 of fastener 220. Upon movement of fork 212 from its intermediate to its distal position, crosshead guide 240 abuts annular abutment 238, allowing outer tubular member 230 and plunger 226 to be moved longitudinally (see FIG. 24) to eject (fire) fastener 220 through segment 244b to penetrate the overlapped end portions of body tissue held between transverse jaw members 158a, 158b. Plunger 226 is subsequently withdrawn to its original position by return of fork 212 to its proximal position.

With continued reference to FIGS. 21 and 24, an alternative fastener cartridge 250 is shown which is adapted to hold a plurality of fasteners 220 for sequential ejection, one at a time in end to end relationship, into body tissue. The body of fastener cartridge 250 is formed of attachable casing halves and is preferably integral with divider 198.

Elongated chamber 254 of cartridge 250 is configured and dimensioned to stack fasteners 220 vertically in face-to-face contacting relationship along their respective longitudinal surfaces. The cross-sectional dimension of chamber 254 is equal to or slightly greater than the major diameter of each rod-like fastener 220 to facilitate a snug fit for each fastener 220 within the chamber.

Fasteners 220 are biased downwardly in chamber 254 by spring 264 and follower 262 (FIGS. 21 and 24), with the lowermost fastener in the segment between bore-like segments 244a, 244b. After each fastener 220 is ejected, plunger 226 is withdrawn longitudinally into segment 244a to allow the next fastener 220 to move into the firing chamber segment as spring 264 exerts a force on follower 262.

Cover 256 is removably fastened to housing 152 by a screw 258. The upper end of spring 264 is retained by a nipple formed on the underside of cover 256, and the lower end of spring 264 is retained in a slot formed in the top portion of follower 262. Removable cover 256 allows access to fasteners 252 and allows the cartridge 250 to be removed and replaced with another loaded cartridge. The new cartridge can optionally contain fasteners of a different size. Elongated window 266 bisects opposite side portions of chamber 254 to allow the position of follower 262 to be visually observed to indicate the remaining number of fasteners 252 (See FIGS. 15 and 25).

Referring to FIGS. 15–19, a pair of handles 154 are shown for moving fork 212 between its proximal and distal positions. Although the handle mechanism is described for use in the embodiment of FIG. 15, it can also be used as an alternative to handles 128 and 130 of the embodiment of FIG. 1 for actuating fork 70. Handles 154 extend generally rearwardly from handle portion 268 and are pivotally connected to handle portion 268 by pivot pins 270 for movement between an open position as shown in FIG. 16, to a closed position as shown in FIG. 18.

Squeezing handles 154 together actuates parallelogram transmission 272 to cause jaws 158 to move to their closed position and plunger 226 to move longitudinally from its retracted position to its extended position to eject and discharge fastener 220. Parallelogram transmission 272 is pivotally connected at opposite ends thereof to handles 154 by pins 274 slidably mounted within elongated slots 276, so that the pivotal motion of handles 154 toward and away from each other allows parallelogram 272 to expand and contract.

Pin 280 connects parallelogram transmission 272 at its proximal end 278 to the handle portion 268 and pin 284 connects transmission 272 at its distal end to drawbar 282. As parallelogram 272 contracts under the influence of the pivotal motion of handles 154, causing its forward end to move longitudinally forward in the direction of arrow 286, longitudinal motion is transferred to drawbar 282 which being connected to fork 212, transfers longitudinal motion thereto. A spring 288 attached between the rear end of drawbar 282 and the handle portion 268 causes drawbar 282 to move rearwardly when handles 154 are released, thus returning fork 212 to its proximal position. Movement of drawbar 282 rearwardly also returns handles 154 to their open position.

Figure 26:
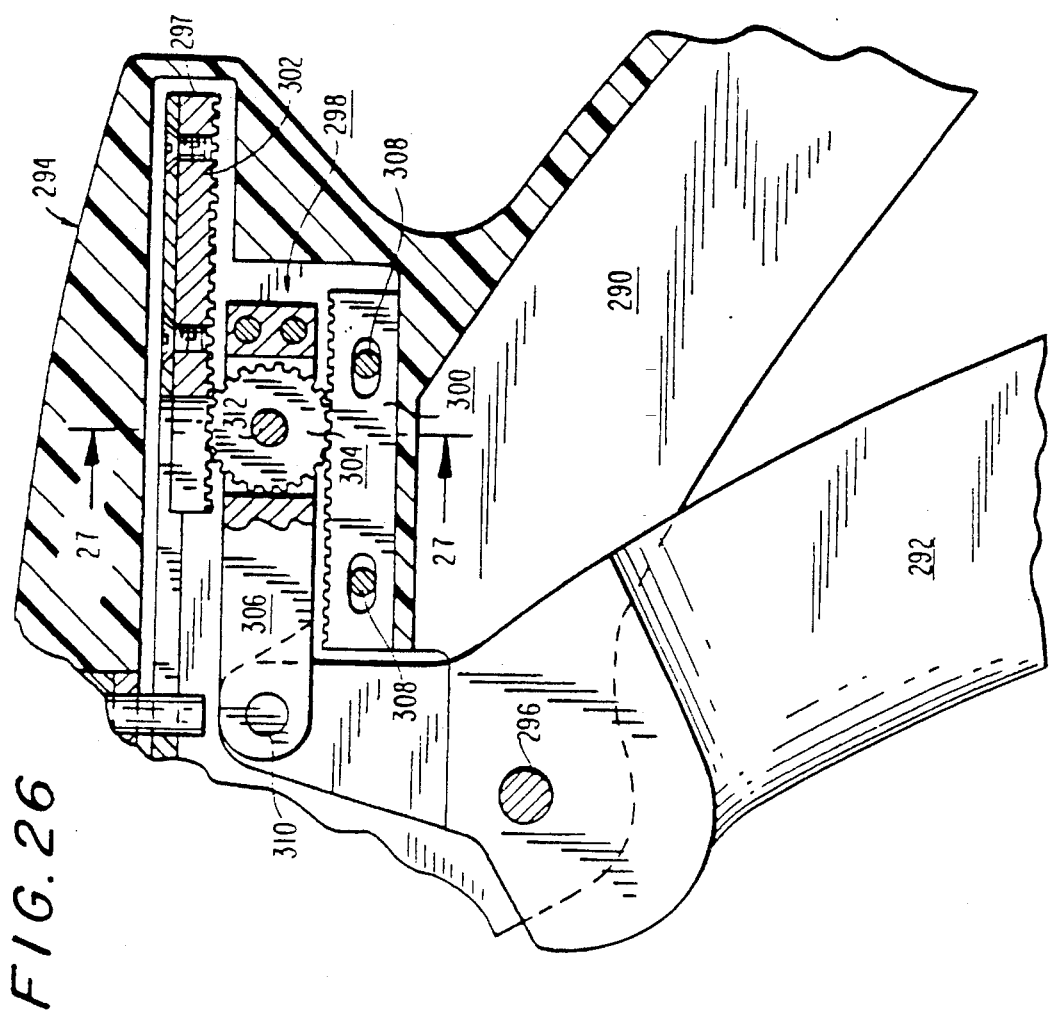
FIG. 26 is a view of an alternative embodiment of a mechanism for closing the pincer jaws and firing the fastener member incorporating a rack and pinion device in a handle section.
Figure 27:
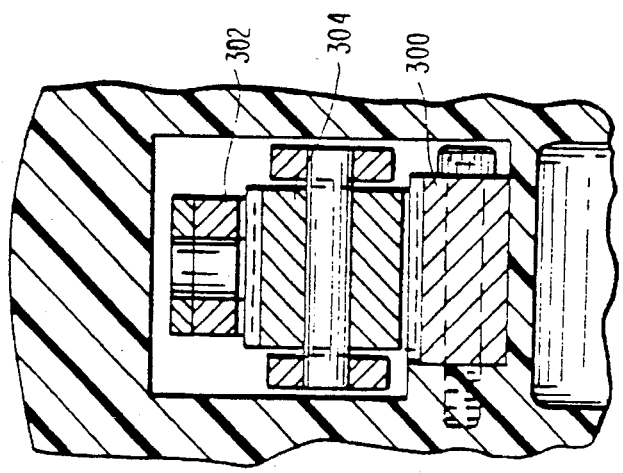
FIG. 27 is a cross-sectional view taken along lines 27—27 of FIG. 26 illustrating the pinion and associated racks.

Referring to FIGS. 26–29, an alternative form of actuating handles are shown which can be utilized with either embodiment of the present invention. Handle 292 is pivotally connected to handle portion 294, and is adapted to pivot about pin 296 from an open position as shown in FIG. 26, toward a closed position adjacent handle 290, as shown in FIG. 29, to move fork 212 to its distal position to thereby close jaws 158 and to move plunger 226 longitudinally to its extended position to discharge fastener 220.

Referring to FIGS. 26–29, rack and pinion assembly 298 translates the pivotal motion of handles 290, 292 to longitudinal motion of fork. Rack and pinion assembly 298 includes a pair of spaced, opposed racks 300, 302, pinion gear 304, and link member 306 which interconnects handle 292 and pinion gear 304. Rack 300 is fixedly secured to handle portion 294 by a pair of cap screws 308 and pinion gear 304 is positioned between racks 300, 302, with its teeth engaged with racks 300, 302. One end of link 306 is pivotally connected via a pin 310 to handle 292 and the other end is attached to pinion gear 304 by a pin 312, about which gear 304 rotates.

Rack 302 is carried within handle portion 294, and is adapted for longitudinal movement therein. As handle 292 is pivoted towards its closed position, link member 306 moves gear 304 distally, as indicated in FIG. 28 by arrow 314. Rack 302 is intermeshed with gear 304 so that rotation of gear 304 causes rack 300 to move longitudinally. As gear 304 moves longitudinally forward along rack 300, gear 304 rotates counterclockwise causing rack 302 to move longitudinally distally. Rack 302 is connectable to fork 212 adjacent its proximal end and transfers longitudinal motion to fork 212 such that fork 212 moves from its proximal position to its distal position.

Spring 297, shown schematically in FIG. 29, attached between the rear end of rack 302 and the rearwardmost extension of handle portion 294, causes rack 302 to move longitudinally rearward when handles 290, 292 are released, thus returning fork 212 to its proximal position. As rack 302 moves longitudinally rearwardly, gear 304 rotates clockwise, and moves proximally rearward along rack 300 causing link 306 to move proximally. Link 306 translates the proximal motion of gear 304 to handle 292, thus returning handle 292 to its open position.

Referring now to FIG. 8, the operative principles of the invention will be described. There is illustrated in phantom the upper surface of skin 316 surrounding an opening 318 such as a wound or surgical incision. The apparatus 10 (or apparatus 148) is positioned such that transverse gripping members 18 are placed generally parallel to the upper surface of the skin, with spaced stabilizers 20, 21 positioned to contact the tissue portions adjacent the proximal and distal ends of griping members 18. Alignment pin 59 is positioned to intersect with opening 318, and apparatus 10 is lowered in the direction of the arrow such that sharp tips of the jaws pierce the skin minimally.

Thereafter, squeezing the handles of the apparatus together moves arms 24 toward each other, closing jaws 12, and causing the sharp tips of the gripping members to intermesh, thus joining the skin portions surrounding opening 318 as shown in FIG. 11, in an at least partially overlapping undulating, or sinusoidal waveform shape, as indicated by phantom lines 56.

At this point, further squeezing of the handles causes plunger 84 to move longitudinally, ejecting the lowermost elongated rod-like fastener longitudinally from the stacked array and into in a position between gripping members 18 and penetrating the overlapped waveform shape to attach the two body tissue portions together (see FIG. 13).

Subsequently, the handles are released, allowing spring 60 to bias arms 24 outwardly, thus returning jaws 12 to their first; open position and allowing their sharp tips to be removed from the body tissue adjacent opening 318. As discussed above, after each fastener is discharged, the next rod-like fastener is biased into the firing chamber segment of chamber 105 under the influence of springs 110.

Depending upon the nature and size of opening 318, one or more fasteners may be discharged in sequence and in adjacent end to end relation, starting at the distalmost segment of the wound and advancing progressively rearwardly to the proximalmost segment of the wound. That is, the apparatus 10 is repositioned rearwardly with its forwardmost stabilizer plate 20 adjacent the rearmost fastener and pin 59 extending into opening 318, and abutting the rearmost end of the previously discharged fastener. Thereafter, squeezing the handles of the apparatus together once again closes jaws 12, causing the sharp tips of the gripping members to intermesh to join the skin segments surrounding opening 318, and causing another fastener to be discharged to penetrate the overlapped waveform shape to attach the two tissue segments. The handles may now be released to return jaws 12 to their first, open position, allowing the sharp tips of jaws 12 to be removed from the body tissue adjacent opening 318.

The apparatus may then be repositioned as necessary in the area adjacent the rearmost inserted fastener to join other segments of opening 318, as described above, until the proximalmost segment of opening 318 is closed. As may be appreciated, the fasteners retain the separate portions of skin in engaged relation such that opening 318 in the skin is prepared for natural permanent healing and adhesion with minimum or no scarring.

The embodiment of FIG. 21 operates in the same manner as described above to close an opening in the body tissue. As is clear, the various handle mechanisms described above can e used to close the jaws and fire the fasteners for either embodiment.

Referring now to FIG. 30, an alternative embodiment of the apparatus of the invention is disclosed. This embodiment incorporates inter alia, the following features:

a) a pair of jaws each having dual pairs of skin gripping tips;

b) a fork and roller system to approximate the jaws with an associated coil spring spreader system;

c) a coil spring system to bias rod-like fasteners toward the firing position;

d) a visual color indicator system to inform the surgeon when the last fastener has been fired;

e) a unitary flexible fork driving system to approximate the jaws and to advance fasteners, utilizing few components; and f) a stabilizer platform for orienting and positioning the apparatus for effective firing of fasteners.

Referring again to FIG. 30, a perspective view of the present embodiment of the apparatus 400 is illustrated. As in the embodiments described hereinabove, jaws 412 are carried by housing 414 which provides an effective support frame for the jaws. The housing may be formed of two parts as shown appropriately adhesively attached or welded together. Handle section 416 is provided and configured for gripping the frame and trigger mechanism 418 is pivotally attached to housing 414 in a manner to be described hereinbelow. This trigger mechanism is arranged to facilitate approximation of the tissue gripping jaws followed by firing of elongated rod-like fasteners in a manner somewhat similar to the manner described hereinabove.

Referring to FIG. 31, the apparatus 400 incorporates a uniquely configured broad-based stabilizer platform 420 which is preferably constructed integrally with the outer housing 414 and which is of dimensions sufficient to assist the surgeon in positioning and orienting the gripper jaws to approximate the tissue portions utilizing the sharp gripping tips 428 as described previously. In particular, the broad based platform advantageously provides a guide to enable the surgeon to position the skin gripping tips 428 at the most favorable angle with respect to the surface of the skin so as to fire the rod-like fasteners in a preferred predetermined orientation and direction. The platform 420 preferably has a generally square configuration as shown. However, other geometric configurations are contemplated to provide sufficient surface area and lateral dimensions to enable the surgeon to place the apparatus against the skin while retaining the approximating jaws 412 in the proper position and orientation. Platform 420 is preferably constructed integrally with the housing and may be made of the same material. One such material is a polycarbonate material such as LEXAN® brand material by General Electric Corporation.

Figure 32:
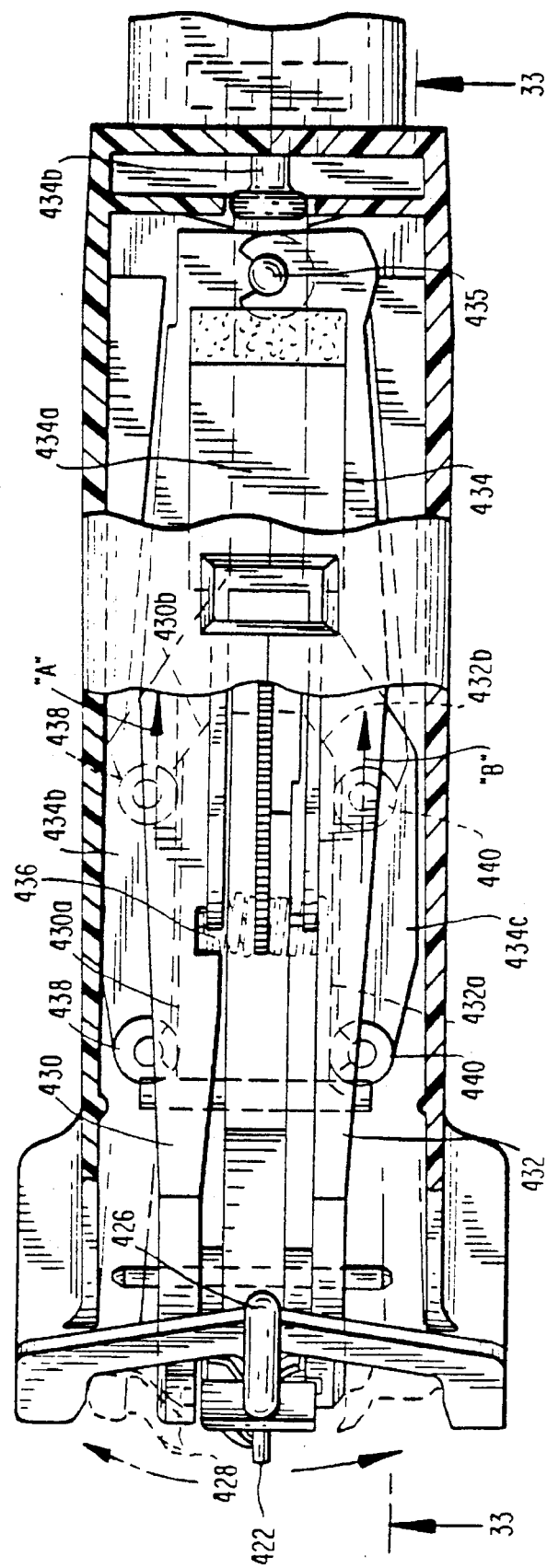
FIG. 32 is an enlarged view partially in cross-section, taken along lines 32—32 of FIG. 30 illustrating the jaw closing mechanism of this embodiment.

Referring now to FIG. 31, in conjunction with FIG. 32, it can be seen that the tissue gripping tips 428 are configured in the present embodiment as dual opposed pairs of sharp tips positioned such that when the jaws are closed for gripping tissue each pair of sharp tips are positioned in adjacent overlapping fashion with the next pair of sharp tips in a somewhat modified interdigitating arrangement. The provision of pairs of dual adjacent sharp tips as shown distributes the approximating forces uniformly over the area of the tissue surrounding the opening.

Referring once again to FIG. 31, in conjunction with FIGS. 32 and 33, locator alignment pin 422 is positioned in housing 424 and biased outwardly of the housing by spring 426 shown schematically in FIG. 33. The pin 422 is intended to perform similarly to alignment pin 59 and 199 in the previous embodiments and serves to provide the surgeon with a device which is readily insertable into the opening in the body tissue after each rod-like fastener is fired so as to enable the surgeon to align the skin-gripping jaws 428 precisely with respect to the opening so as to make certain that firing of the fastener is as central to the tissue opening as is possible. At a point when substantially the entire opening with tissue has been fastened and a small unfastened portion remains, completion of the closure may be accomplished with one more rod-like fastener. In such case, alignment pin 422 will encounter resistance against the sealed position, causing spring 426 to be compressed to retract alignment pin 422 to permit gripper jaws 428 to grip the remaining portion of the opening for fastening thereof.

Referring now to FIG. 32, there is shown a view partially in cross-section taken along lines 32—32 of FIG. 30 in which an alternative arrangement is provided for closing the jaws and for biasing the jaws toward the open position. Jaws 428 are attached to the distal ends of arms 430, 432 which are pivotally connected at pin 434 as shown. Arms 430, 432 are pivotally connected by pin 436 and are biased away from each other by coil spring 436, each end of which is attached to a respective inner surface portion of each arm 430, 432 as shown. The normally—or open—rest position of the jaws is as shown in solid lines in FIG. 32. The manually operable jaw approximating and firing system which is supported within handle section 416 of housing 414 as will be described hereinbelow, is connected to yoke 434 having central shaft 434a and yoke arms 434b and 434c extending outwardly therefrom as shown. Each support arm 434b, 434c rotatably supports roller 438 and 440 respectively at the distal end as best shown in FIG. 32. When yoke 434 is advanced distally from the initial proximal position the rollers 438, 440 engage and ride up camming surfaces 430b, 432b causing spring biased arms 430 and 432 to be approximated toward each other so as to cause the jaws 412 to move to the closed position shown in FIG. 31. Thereafter rollers 438, 440 engageably roll along grooved surfaces 430a, 432a to complete the approximation of the jaws 412.

To open the jaws 412 to the open positions shown in dotted lines in FIG. 32, yoke 434 is withdrawn in the direction illustrated by arrows A & B in FIG. 32 to a proximal position until the rollers 438, 440 reach ramped surfaces 430b and 432b shown in dotted lines in FIG. 32. When the rollers 438, 440 are moved to a position proximal of surfaces 430a, 432a, and are disengaged from the pivotal arms 430, 432, resilient spring 436 causes the arms to move outwardly from each other causing the gripper jaws 412 to move away from each other toward the open position shown in dotted lines in FIG. 32.

Referring now to FIG. 33 in conjunction with FIG. 32, the fastener support cartridge 442 for storing rod-like fasteners 444 in position for firing is shown. This cartridge 442 may be disposable with the instrument, or it may be removable and replaceable. Further, if the cartridge 442 is structured to be removable, it is contemplated that the cartridge may either be disposable or refillable with fasteners.

The rod-like fasteners 444 are biased toward the firing position at the lower portion of the cartridge 442 by follower bar 446 which is biased downwardly toward the firing position by coil spring 448 as shown in FIG. 33. Thus, each rod-like fastener 444 is fired out of opening 450 located immediately proximal of the jaws and into the body tissue for fastening. At this point, the entire stack of rod-like fasteners is automatically moved downwardly under pressure of coil spring 448 to position the next rod-like fastener in line for firing through opening 450. The coil spring 448 is suitably supported as shown and is constructed of a material and has a spring rate which facilitates the continuous application of downward pressure on the fastener follower 446 until the last fastener has been fired as is shown in FIG. 36.

Figure 35:
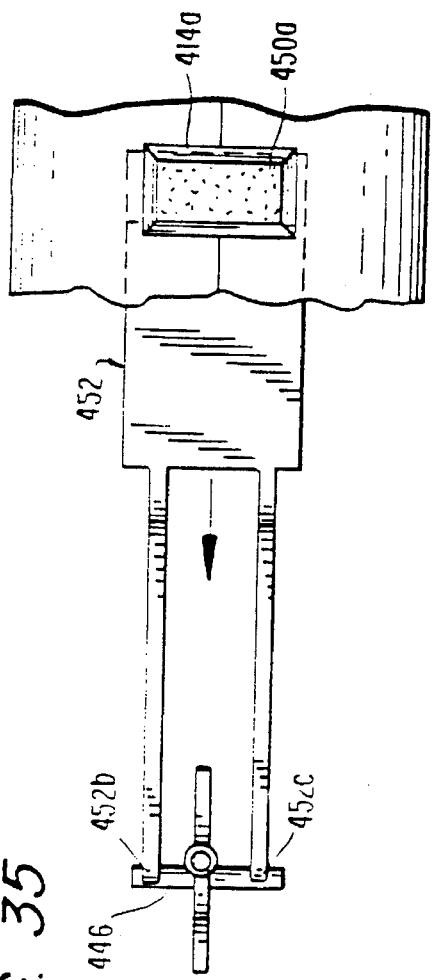
FIG. 35 is a view from above of the system for providing color indication when the last rod-like fastener has been fired.
Figure 36:
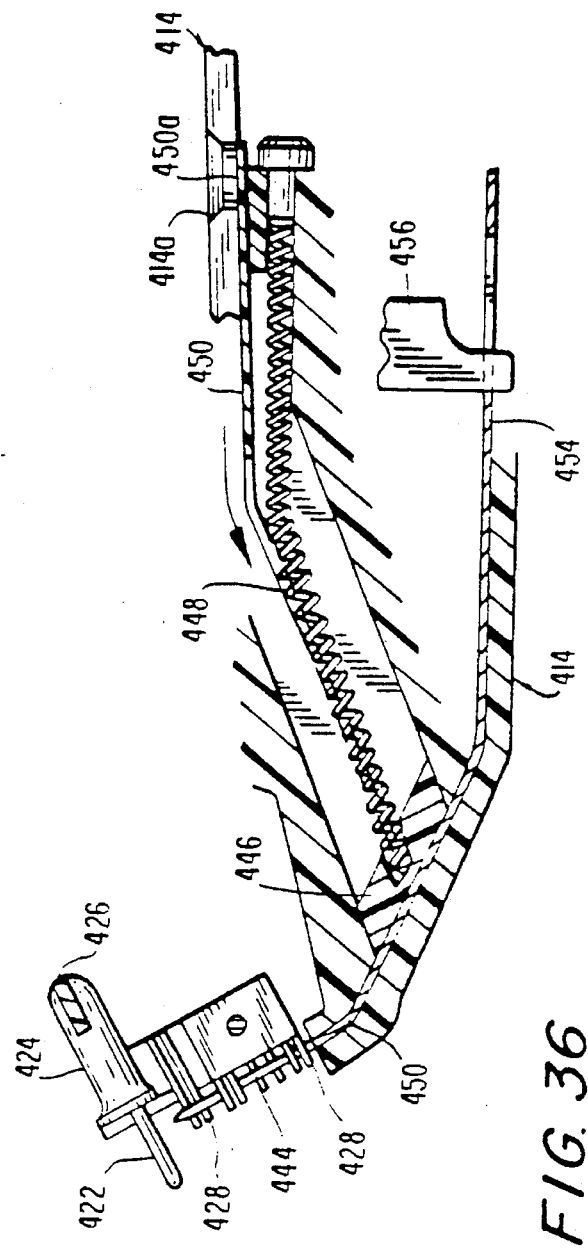
FIG. 36 is a view partially in cross-section of the cartridge for storing rod-like fasteners after the last fastener has been fired.

A visual indicator flag 452 shown in FIGS. 33, 35 and 36 is positioned above coil spring 448 and is attached at 452b and 452c to fastener follower bar 446 as shown in FIG. 35 in a manner such that the flag 452 moves in a downwardly distal direction as the fastener follower bar 446 is advanced progressively downwardly as each fastener is fired. The proximal end portion of flag 452 contains an area 452a which is brightly colored (i.e. yellow) and which begins appearing behind open window 414a in housing 414 when a predetermined number of fasteners have been fired. Ultimately, the entire rectangular brightly colored portion 450a of the flag fully appears in window 414a after the last fastener has been fired. The flag 452 is flexible and is adapted to move distally and conform to the gradually curved configuration of coil spring 448 as the fasteners are fired. The flag may be made of a thin plastic sheet, for example. Initially, the major portion of the flag 452 is straight as shown in FIG. 33. Furthermore, the length of the flag 452 in relation to the position of the brightly colored area 450a is determined such that the brightly colored area appears within window 414a after the last fastener has been fired. Also, the flag 452 and window 414 may contain calibrated markings to provide indication to the surgeon of the number of fasteners remaining in the cartridge at any time corresponding to the location of the flag.

Referring now to FIG. 34 in conjunction with FIG. 33, an alternative system for firing the fasteners is embodied in firing plate 454 which is positioned within an appropriate space provided in the lower portion of housing 414 as shown in FIG. 33. Fastener firing plate 454 contains a rectangular opening 454a for reception of firing bar 456 which is attached to yoke 434. Thus, when yoke 434 is advanced distally by the mechanism contained within housing 414 as will be described hereinbelow, firing rod 456 advances distally from its initial rest position, i.e. against proximal edge of rectangular opening 454a, until it engages the distal wall of opening 454a at which point advancement of fastener firing plate 454 toward rod-like fasteners 444 begins. Prior to engagement of the fastener firing rod 456 with the distal edge of opening 454a of firing plate 454 the movement of firing bar 456 between the two edges of opening 454a represents corresponding movement of the yoke 434 between the open jaw and the closed jaw positions. Thus, at the point when firing bar 456 engages the distal edge of plate opening 454a and begins advancing plate 454 distally to fire the next in line rod-like fastener, the rollers 438 are at their proximal location shown in dotted lines in FIG. 32 and the jaws 428 are closed. The remaining distal movement of yoke 434 causes the plate 454 to fire the next-in-line fastener 444 through opening 450 while rollers 438 are advanced from the proximal positions shown in dotted lines in FIG. 32 to the distal positions shown in solid lines in FIG. 32. During this latter movement the jaws 412 are closed, except that the distal position of the rollers provides somewhat greater, or more positive closing force on the jaws due to their relative distal location.

Thus, when the body tissue is initially gripped between the sharp gripping tips 428 of jaws 412, the jaws are then approximated by the movement of the yoke 434 and the engagement by rollers 438, 440 with the engaging surfaces 430a and 432a of jaw supporting arms 430 and 432. The approximation of the sharp tips 428 of jaws 412 causes the body tissue to assume the undulating pattern around the opening as described in connection with the previous embodiments. Continued advancement of the yoke causes firing of the fastener to the body tissue as described.

The fastener is moved distally through the lowermost opening 450 in housing 414 by the force of elongated fastener firing pin 454b which extends distally of the plate 454. The rod-like fasteners are preferably of a bio-absorbable material as noted previously. The fasteners are elongated and preferably have a rectangular cross-sectional configuration. The fasteners also are flexible and resilient and therefore are capable of passing through the curve of opening 450. Furthermore, fastener plate 454 is also preferably made of a super elastic material such as TINEL brand metal available from Raychem Corporation, Menlo Park, Calif. and is therefore sufficiently resilient to follow the curved path of the fastener. In order to assist this firing step the distal portion of fastener firing pin 454b is straight over the major portion of its length and contains a slight curvature as shown in FIG. 34 and is sufficiently flexible to facilitate passage through the curved portion of aperture 450. Alternatively, the fastener firing plate may be constructed of other super-elastic materials such as NITINOL brand metal. Hardened, yet flexible steel, or even plastic, are also contemplated.

In summary, it can be appreciated that when the apparatus is fired by squeezing trigger 418 toward handle 416 a forward force is transmitted to yoke 434. This force provides a two-step function as follows:

1. Approximation of the gripper jaws 428 toward each other in order to approximate the body tissue surrounding the opening and gripped by sharp tips 428; and
2. Thereafter, firing of the rod-like fastener into the body tissue at the undulating interface created by the approximated jaws.

Figure 37:
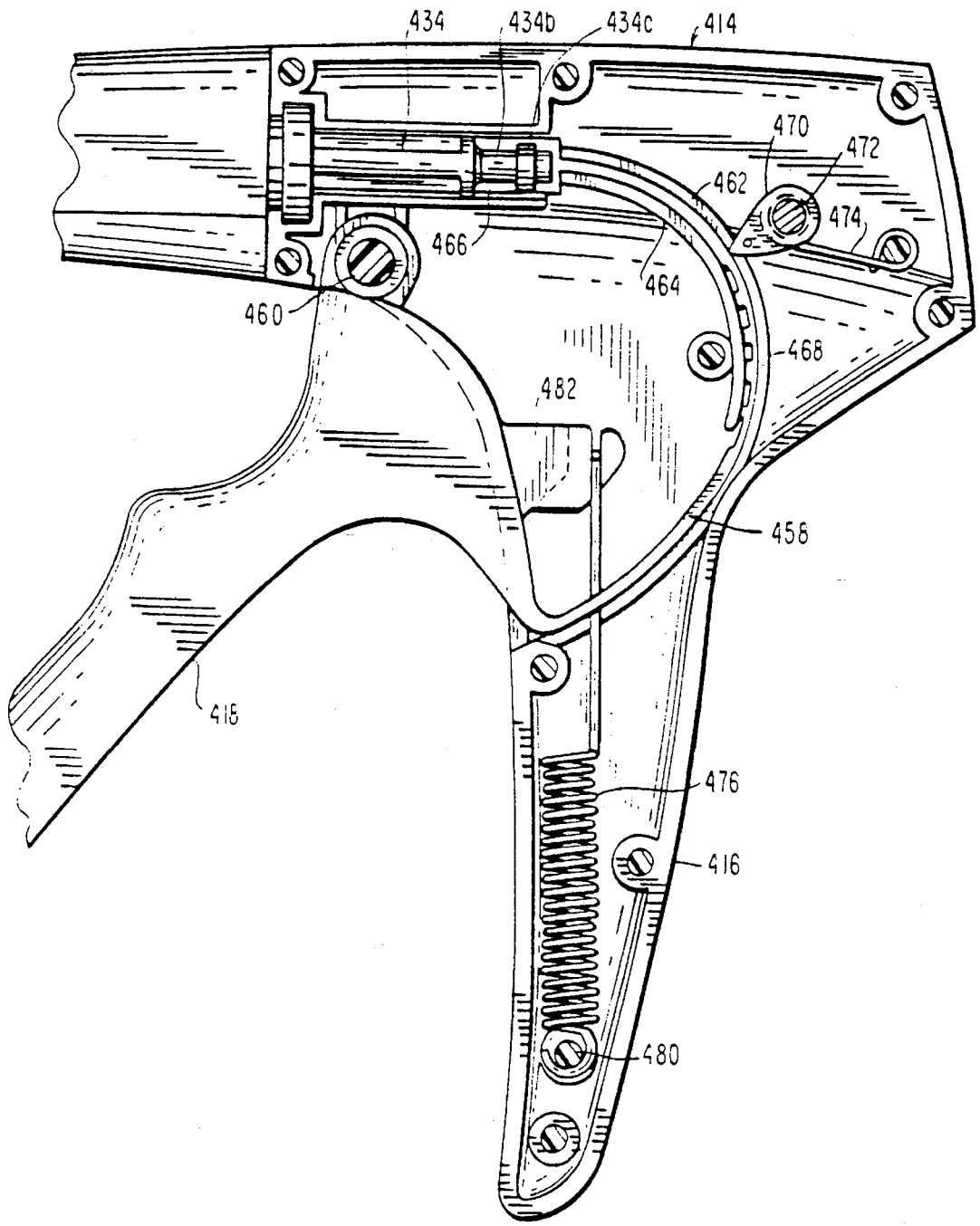
FIG. 37 is a view taken along lines 37—37 of FIG. 30, illustrating an alternative structural arrangement in the handle for mechanically closing the jaws and for firing rod-like fasteners at the distal end of the apparatus with the trigger in the open position.

Referring now to FIGS. 37–42, the mechanism supported by housing 414 for providing the requisite distal force on yoke 434 for approximating the jaws and sharp gripper tips and for thereafter firing the rod-like fasteners into the body tissue will now be described. Supported by and contained within housing 414 is a flexible strap 458 connected to trigger 418 which is pivotally mounted to housing 414 by pin 460. Flexible strap 458 is arranged to be slidably supported within curved tracks 462 and 464 and includes at the distal end portion cylindrical connector member 466 which contains an appropriately configured opening 466a for reception and attachment of the proximal shaft 434b of yoke 434. The connection between the flanged aperture 466a of connector 466 and the flange 434c of shaft 434b is as shown in FIG. 37, accomplished by inserting shaft 434b into the central slot 466b shown clearly in FIG. 39. Disc-like head 434c is thus connected to connector 466 to connect shaft 434b to connector 466. This connection causes yoke 434 to move distally with connector 466 when the trigger 418 is squeezed. Thus, when the connector moves distally shaft 434b and yoke 434 moves distally and when the connector moves proximally shaft 434b and yoke 434 moves proximally.

Figure 38:
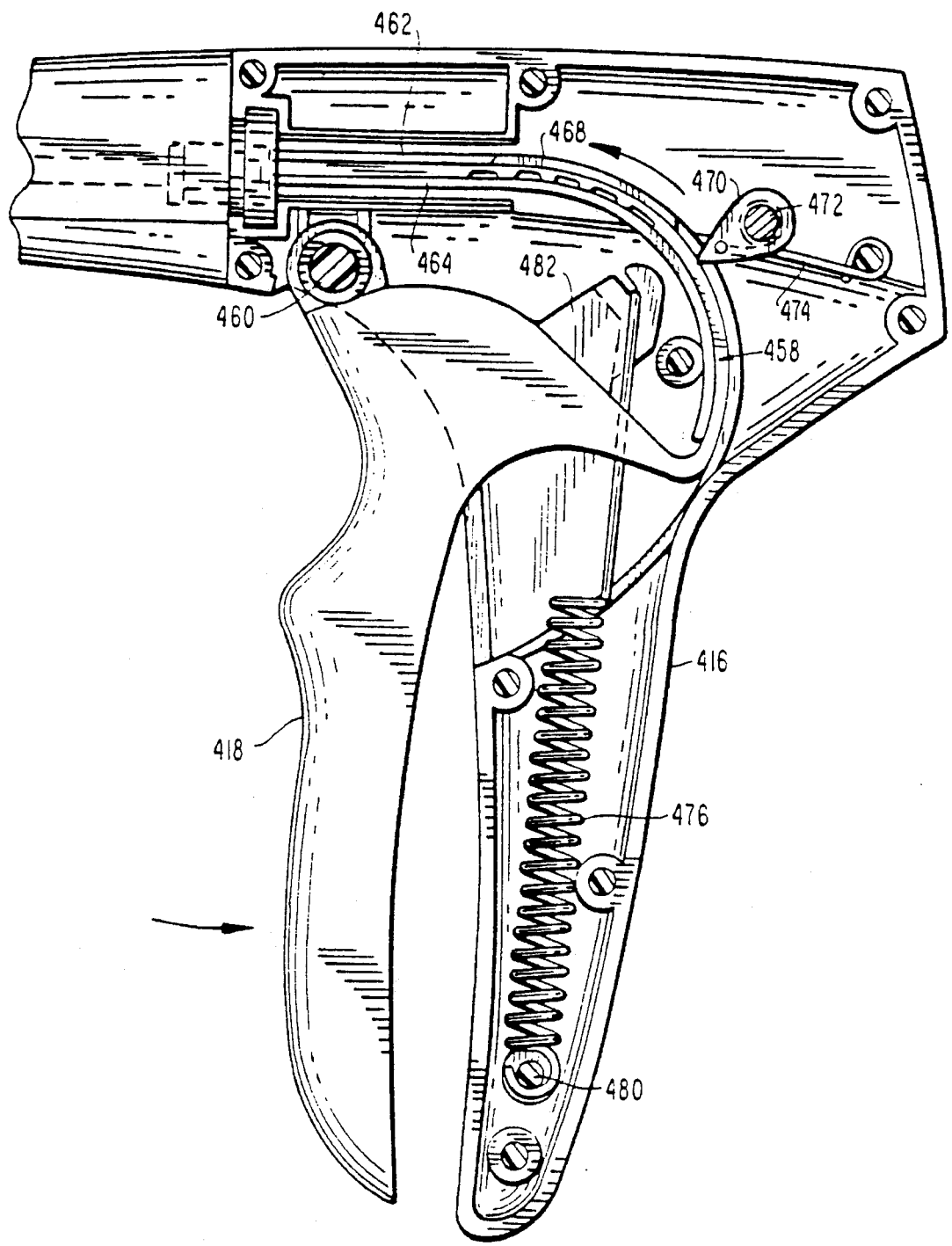
FIG. 38 is a view similar to FIG. 37 illustrating the jaw closing mechanism supported in the proximal portion of the housing of the apparatus with the trigger in the fully squeezed position.
Figure 39:
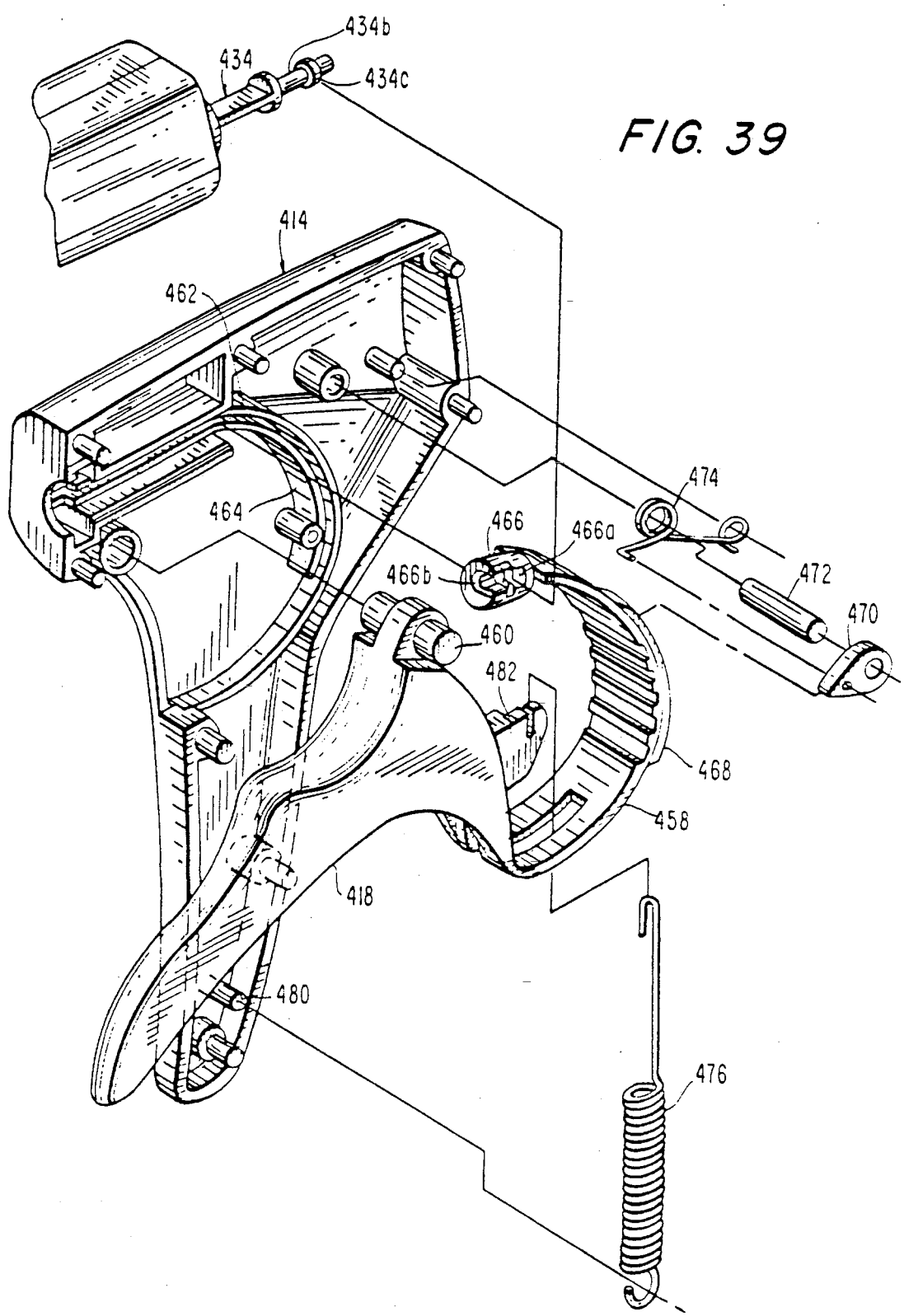
FIG. 39 is a perspective view with parts separated for convenience of illustration of the jaw closing and fastening mechanism of FIGS. 37 and 38.

Flexible strap 458 may be of flexible metal construction or of any flexible material of sufficient strength to transfer forces to yoke 434. Such alternative materials such as LEXAN brand polycarbonate or the like may be used. As best shown in FIG. 38, the flexible strap 458 contains a raised nylon pad 468 which is flexible and resilient and thus engageable by pawl 470 which is pivotally mounted on shaft 472 and biased toward counterclockwise rotation by spring 474. Nylon pad 468 functions as a ratchet plate as will be described.

Elongated coil spring 476 is connected at one end to pin 480 and at the other end to slotted connector flap 482 which is integrally connected to trigger 418 such that when assembled, pivotal movement of trigger 418 toward hand grip 416 is resisted by the bias of spring 476 as shown. Thus, manually squeezing trigger 418 toward handle grip portion 416 causes spring 476 to become extended as shown particularly in FIG. 38 against the bias of the trigger 418. The normal bias on trigger 418 by spring 476 is toward the rest position shown in FIG. 37.

Referring now to FIGS. 37 and 38, squeezing of trigger 418 toward hand grip 416 causes flexible strap 458 to advance about the curved path defined between support tracks 462 and 464 causes the distally positioned connector 466 to move in the distal direction with the strap 458. As the strap 458 advances distally within the space defined by curved tracks 462 and 464, the resilient nylon pad engages pawl 470 which is pivotally mounted on shaft 472 and biased counterclockwise by spring 474.

During advancement of strap 458, should the operator discontinue the trigger motion for fastener aligning purposes or otherwise, the constant bias of spring 476 on trigger 418 causes strap 458 to retrace a small proximal distance until the tip 470a of pawl 470 forcefully engages the nylon pad 468 and the spring force causes the tip of pawl 470 to create a slight indentation as best shown at 468a in FIG. 40. This flexible resilient engagement of the pawl 470 with nylon pad 468 creates a jamming of the pawl 472 and nylon ratchet pad 468 prevents further reverse movement of the strap 458. Thereafter, when the surgeon resumes the tissue approximating and firing sequence the trigger 418 is simply pulled further proximally toward handle grip 416 until the jaws have been fully approximated and the elongated rod-like fastener has been fired as described hereinabove. At this stage of the sequence, nylon pad 468 will have already passed pawl 470 as shown in FIG. 38 thus discontinuing the interaction between the pawl 470 and the nylon pad 468. When the trigger is released and permitted to return to its rest position as shown in FIGS. 30 and 37, the trigger is naturally biased by coil spring 476 and pawl 470 is permitted to assume a downwardly sloped orientation under the bias of spring 474. Also a downward force is provided on the tip 470a of the pawl 470 by the downward movement of the strap 458 engaging and passing the tip 470a of the pawl 470. Thereafter, the next tissue approximating and fastener firing sequence may be repeated as described hereinabove.

Referring now to FIGS. 43–47 another alternative embodiment of a tissue approximating system is illustrated. The apparatus 500 is shown in FIG. 43 and includes housing 514 with hand grip 516 and trigger 518 for approximating the body tissue surrounding an opening and for firing rod-like fasteners in a manner similar to the embodiments previously described. The apparatus shown in FIG. 43 incorporates an alternative tissue approximating system as shown in FIGS. 44–47 as will be described.

Referring now to FIG. 44, tissue approximating arms 530 and 532 are pivotally connected to each other by associated flanges 530a and 532a through which pivot pin 531 extends. Pivot pin 531 supports wire-like spring 534 via loop 534a extending around the pin 531. The spring 534 is arranged to bias tissue approximating arms 530, 532 pivotally away from each other at the portions distal of the pivot pin 531 and in the portions proximal of the pin 531 the portions of arms 530, 532 are biased toward each other as shown. The arms 530, 532 resemble a spring-type clothes pin.

Figure 47:
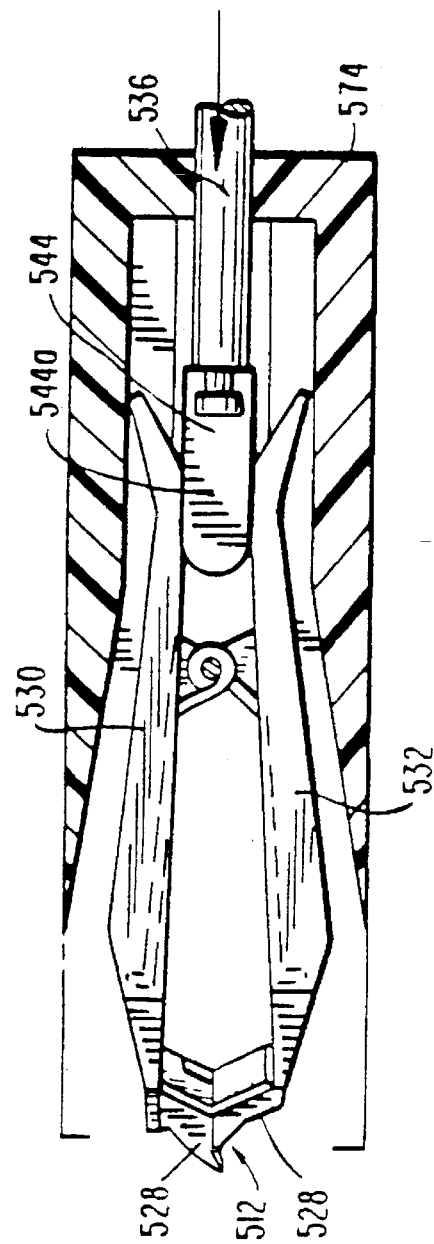
FIG. 47 is a view from above illustrating the jaw closing mechanism of the embodiment of FIG. 43, when the jaws are in the closed position.

Referring now to FIGS. 44–47, a linear gear-type arrangement is provided in the form of elongated rack 536 having a circular cross-section and a plurality of individual circular teeth 536a is provided as shown. Trigger 518 is pivotally mounted to housing 414 via pivot pin 538 and contains a plurality of upstanding teeth 540 extending over arcuately shaped surface portion 542 of drive member 541. Teeth 540 of arcuate drive member 541 are dimensioned to mesh and interengage with teeth 536a of rack 536. When trigger 518 is pulled manually toward hand grip 516 arcuate drive member 541 rotates counterclockwise and teeth 540 associated therewith interengage the teeth 536a of rack 536 causing rack 536 to advance distally until the distal member 544 engages the proximal end portions of tissue approximating arms 530 and 532. Continued squeezing of trigger 518 toward hand grip 518 causes continued advancement of the distal member 544 connected to rack 536 to actually engage ramped surfaces 530b, 532b to cause the proximal portions of tissue approximating arms 530, 532 to spread apart as shown in FIG. 47. This movement causes the distal portions of the approximating arms 530, 532 to move toward each other. This movement causes the skin approximating sharp tips 528 of jaws 512 to move to a somewhat interdigitated position (i.e. adjacent opposed, and partially overlapped positions as best shown in FIG. 31) to grip tissue as noted and described in connection with the previous embodiment. It can be seen that elongated rack 536 and upstanding teeth 540 of drive member 541 essentially function in a manner similar to a linear version of a set of rotary gears.

Figure 45:
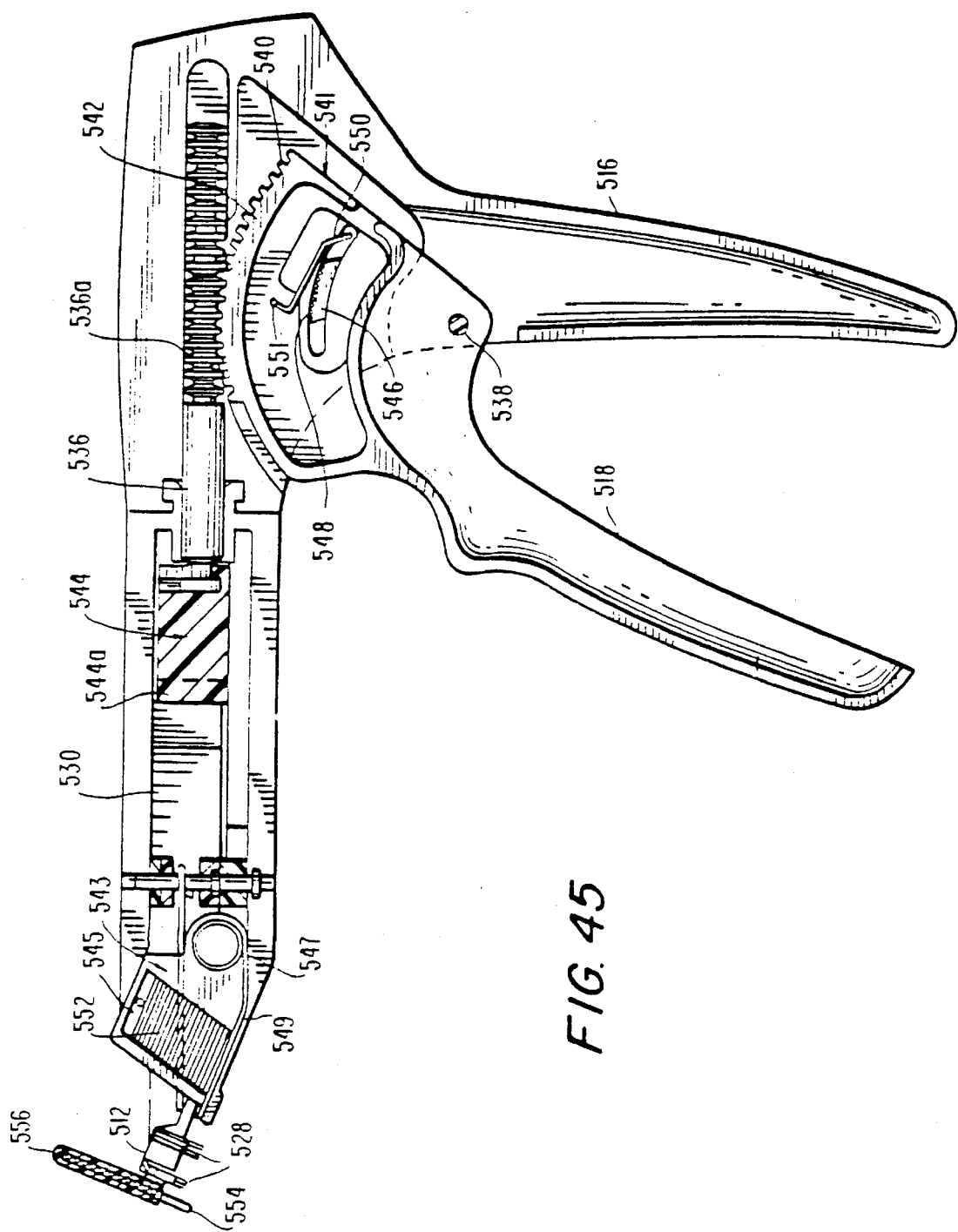
FIG. 45 is a view taken along lines 45—45 of FIG. 44 illustrating a side view of the jaw closing and fastener firing mechanism of FIG. 44.

As seen in FIGS. 44, 45 and 47, the distalmost tip of the distal portion of tissue approximating drive member 544 is arcuately shaped. The surfaces 530b and 532b of the tissue approximating arms 530, 532 are sloped and oriented to receive the arcuate distal surface of drive member 544 as shown in FIGS. 44 and 47. Thus, the engagement of the arcuate distal surface of drive member 544 with the tissue approximating arms 530, 532 is facilitated by gradual movement of member 544 up the ramped surfaces 530b, 532b, and the approximation of the distal movement of the arms is facilitated by forces operative counter to resilient spring 534.

Fastener cartridge 543 is removable and replaceable and stores rod-like fasteners 552 biased downwardly by spring loaded follower 545. Fastener ejection is accomplished directly by coil spring 547 which functions as a pusher plate and which is biased proximally by spring action. Thus, spring 547 may be advanced distally by a pusher system similar to the previous embodiments. After firing the fastener and release of the firing system, the pusher mechanism will return to its original position under bias of spring 547. Alternatively, spring 54, may be attached to a separate pusher plate which will operate in a manner similar to the embodiment shown.

In order to enable the surgeon to discontinue the tissue approximating motion for purposes of alignment and/or orientation of the fastener, trigger 518 contains an arcuate shaped member 546 which contains a plurality of ratchet teeth 548 along the upper arcuate surface as shown. The teeth are arranged for engagement by leaf spring 550 (shown in side view only) which is connected to housing 514 by pin 551 and biased downwardly toward teeth 548.

In operation the surgeon positions the jaws 512 against the opening in the body tissue to cause sharp tips 528 to grip the tissue straddling the opening and then squeezes the trigger 518 sufficiently proximally toward hand grip 516 to cause engagement between the wire-like spring 550 until teeth 548 of arcuate member 546. Thereafter, proximal squeezing motion of the trigger may be discontinued for fastener alignment or other purposes while the trigger is retained in the partially squeezed position. After perfecting the position and orientation of the jaws 512, continued proximal motion of the trigger 518 is resumed to complete the tissue approximating and fastener firing sequence. At the completion of the stroke, the ratchet teeth 548 ultimately advance to a position distal of the spring 550 and the spring 550 drops to a disengaged position. The spring 550 and drive member 542 may be arranged by known means to permit the trigger to return to its unloaded initial position in preparation for the next firing sequence as described hereinabove. For example, a ramped surface may be provided to displace spring out of interference with arcuate member 546 to permit trigger 518 to pivot distally to its initial position. Alternatively, leaf spring 550 may contain an aperture through which arcuate member 546 may pass to permit trigger 518 to return to its initial position without interference from arcuate member 546.

Figure 46:
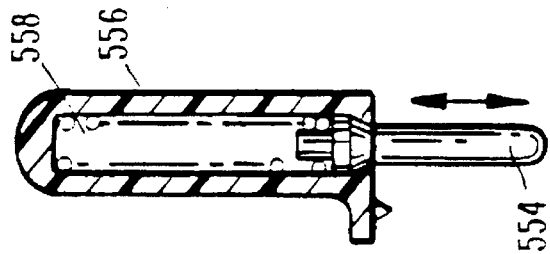
FIG. 46 is a view taken along lines 46—46 illustrating the locator pin located distally of the jaws.

Referring to FIG. 46 in conjunction with FIG. 43 alignment pin 554 is provided within housing 556 and spring biased outwardly by resilient spring 558 in a manner identical to the alignment pin 422 described in connection with the previous embodiments. The structure and operation of the alignment pin 554 is identical to the structure and function of the alignment pin described hereinabove with the previous embodiment.

The function and operation of the apparatus is shown in FIGS. 43–47 is identical to the embodiments described previously. It can be appreciated that this embodiment utilizes a reduced number of components.

Although the embodiments herein contemplate subcuticular attachment of cutaneous matter, it is within the scope of the invention to apply such rod-like fasteners at subcutaneous levels, i.e. below the epidermis and dermis. As may be further appreciated, the jaws, fork, divider and cartridge may be provided as an assembly which is slid longitudinally into the elongated hollow of the housing, and therein retained by suitable means such as a screw. Also, as noted, the fastener cartridge may be either permanently attached or it may be removable and replaceable.

While the invention has been particularly shown and described with reference to the preferred embodiments, it will be understood by those skilled in the art that various modifications and changes in form and detail may be made therein without department from the scope and spirit of the invention. Accordingly, modifications such as those suggested above, but not limited thereto, are to be considered within the scope of the invention.

What is claimed is:

1. A surgical apparatus for attaching at least two end portions of cutaneous body tissue adjacent an opening which comprises:

a) a support frame;

b) a pair of elongated members pivotally attached at proximal end portions thereof;

c) a jaw attached to the distal end of each elongated member, each jaw supporting a plurality of sharp tissue engaging members, the tissue engaging members on each jaw generally facing the tissue engaging members on the other jaw such that when the elongated members are pivoted such that the distal ends move toward each other, the tissue engaging members face each other in generally opposed adjacent relation;

d) a fastener cartridge adapted to store a plurality of rod-like fasteners in stacked relation, the lowermost fastener positionable adjacent an opening through which the fasteners may be individually advanced generally distally;

e) at least one handle pivotally attached to the frame and pivotal toward and away from the fixed handle;

f) a rack having a plurality of teeth; and g) a drive member operative with the pivotal handle and having a plurality of teeth dimensioned and adapted to mesh with the teeth of the rack and arranged for engagement with the teeth of the rack such that when the pivotal handle is pivoted toward the fixed handle, the engagement of the teeth of the rack by the teeth of the drive member causes the rack to move distally.

2. The surgical apparatus according to claim 1 further comprising a first fixed handle fixed with respect to the support frame.

3. The surgical apparatus according to claim 2 further comprising a first coil spring positioned between the elongated pivotal members and adapted to bias the members and the distal ends of the jaws away from each other.

4. The surgical apparatus according to claim 3 further comprising a second coil spring positioned and adapted to engage a fastener biasing member to bias the fasteners toward the fastener firing opening.

5. The surgical apparatus according to claim 4 further comprising yoke means supporting a pair of rollers and adapted for movement distally whereby the rollers engage respective surface portions of the elongated members in a manner to approximate the members and the jaws and movable proximally whereby the members and the jaws are permitted to move away from each other under the bias of the first spring.

6. The surgical apparatus according to claim 5 further comprising a flexible flag attached to the fastener biasing member and extending proximally therefrom prior to firing the first fastener and adapted to advance distally as the fasteners are fired, the flag having a distinctive visually observable portion adapted to appear through an aperture in the support frame after a predetermined number of fasteners have been fired to provide visual indication thereof.

7. The surgical apparatus of claim 6 wherein the rack is attached to the yoke means to cause the jaws to approximate.

8. The surgical apparatus of claim 7 further comprising a fastener drive plate and means to advance the fastener drive plate into driving engagement with the lowermost fastener when advanced distally.

9. The surgical apparatus of claim 8 wherein the yoke means includes a member adapted to be advanced into engagement with the fastener drive plate to drive the lowermost fastener through the fastener aperture when the yoke means is advanced distally.

10. The surgical apparatus of claim 9 wherein the cartridge is removable and replaceable.

11. A surgical apparatus for attaching at least two end portions of cutaneous body tissue adjacent an opening which comprises:

a) a support frame;

b) a pair of elongated members pivotally attached at proximal end portions thereof;

c) a jaw attached to the distal end of each elongated member, each jaw supporting a plurality of sharp tissue engaging members, the tissue engaging members on each jaw generally facing the tissue engaging members on the other jaw such that when the elongated members are pivoted such that the distal ends move toward each other, the tissue engaging members face each other in generally opposed adjacent relation;

d) an elongated fastener positioned to be directed generally medially of the body tissue interface to attach the opposed portions of the body tissue;

e) a yoke supporting a pair of rollers and adapted for movement distally whereby the rollers engage respective surface portions of the elongated members in manner to approximate the members and the jaws and movable proximally whereby the members and the jaws are permitted to move away from each other under the bias of the first spring;

f) at least one handle pivotally attached to the frame and pivotal toward and away from the fixed handle; and g) a rack and associated drive member attached to the pivotal handle and adapted to move distally when the pivotal handle is pivoted.

12. The surgical apparatus according to claim 11 further comprising a first fixed handle fixed with respect to the support frame.

13. The surgical apparatus of claim 12 wherein the rack is attached to the yoke to cause the jaws to approximate.

14. The surgical apparatus of claim 13 further comprising a fastener drive plate and means to advance the fastener drive plate into driving engagement with the lowermost fastener when advanced distally.

15. The surgical apparatus of claim 14 wherein the yoke includes a member adapted to be advanced into engagement with the fastener drive plate to drive the lowermost fastener through the fastener aperture when the yoke is advanced distally.

16. The surgical apparatus of claim 15 wherein the fastener is stored in a cartridge which is removable and replaceable.

17. A surgical apparatus for attaching at least two portions of body tissue, which comprises:

a) a pair of support members;

b) tissue gripping means supported at the distal end of each of the support members;

c) body tissue engaging means extending from each jaw and facing the opposed jaw, the body tissue engaging means being structured and adapted to engage respective opposed portions of the body tissue whereby movement of the jaws toward each other causes the opposed portions of body tissue to be displaced toward each other and engage at the interface thereof so as to assume an irregular shape;

d) elongated fastener means supported proximally of the jaws and positioned to be directed generally medially of the body tissue interface to attach the opposed portions of the body tissue;

e) rack means and associated drive means adapted to move the rack means distally and proximally, the rack means adapted to cause the pair of support members and the body tissue gripping members to move toward each other to grip body tissue when moved distally by the drive means.

18. The surgical apparatus of claim 17 wherein resilient means is positioned between the support members to bias the support members and the jaws in opposed directions.

19. The surgical apparatus of claim 18 wherein the resilient means is a coil spring.

20. The surgical apparatus according to claim 19 further comprising yoke means supporting a pair of rollers and adapted for movement distally whereby the rollers engage respective surface portions of the elongated members in a manner to approximate the members and the jaws and movable proximally whereby the members and the jaws are permitted to move away from each other under the bias of the resilient means.

21. The surgical apparatus of claim 20 wherein the rack is attached to the yoke means to cause the tissue gripping means supported at the distal end of each of the support members to approximate.

22. The surgical apparatus of claim 21 further comprising a fastener drive plate and means to advance the fastener drive plate into driving engagement with the lowermost fastener when advanced distally.

23. The surgical apparatus of claim 22 further comprising a cartridge for supporting the elongated fastener means.

24. The surgical apparatus of claim 23 wherein the cartridge supports a plurality of the fastener means.

25. The surgical apparatus of claim 24 wherein the yoke means includes a member adapted to be advanced into engagement with the fastener drive plate to drive the elongated fastener means through a fastener aperture when the yoke means is advanced distally.

* * * * *